US010717863B2

(12) United States Patent
Ba et al.

(10) Patent No.: US 10,717,863 B2
(45) Date of Patent: Jul. 21, 2020

(54) MUCOADHESIVE AND/OR SOL-GEL CO-HYDROGEL SYSTEMS INCLUDING FLUOROALKYLATED ($R_f$) POLYETHYLENE GLYCOL (PEG) AND $R_f$-PEG-POLY(ACRYLIC ACID) (PAA) COPOLYMERS, AND METHODS OF MAKING THE SAME AND OF DRUG DELIVERY USING THE SAME

(71) Applicants: Yong Ba, Monrovia, CA (US); Yang Sun, Orange, CA (US)

(72) Inventors: Yong Ba, Monrovia, CA (US); Yang Sun, Orange, CA (US)

( * ) Notice: Subject to any disclaimer, the term of this patent is extended or adjusted under 35 U.S.C. 154(b) by 0 days.

(21) Appl. No.: 16/197,186

(22) Filed: Nov. 20, 2018

(65) Prior Publication Data

US 2019/0153213 A1 May 23, 2019

Related U.S. Application Data

(60) Provisional application No. 62/589,311, filed on Nov. 21, 2017.

(51) Int. Cl.
 *C08L 53/00* (2006.01)
 *C08L 101/04* (2006.01)
 (Continued)

(52) U.S. Cl.
 CPC ............ *C08L 53/005* (2013.01); *A61K 9/006* (2013.01); *A61K 9/06* (2013.01); *C08F 293/005* (2013.01);
 (Continued)

(58) Field of Classification Search
 None
 See application file for complete search history.

(56) References Cited

U.S. PATENT DOCUMENTS

2009/0215097 A1* 8/2009 Itai .................. C08F 210/00
 435/11
2014/0371410 A1* 12/2014 Jan .................. C07C 271/24
 526/246

FOREIGN PATENT DOCUMENTS

WO 9801478 A1 1/1998

OTHER PUBLICATIONS

Giyoong Tae et al.; "Hydrogels with Controlled, Surface Erosion Characteristics from Self-Assembly of Fluoroalkyl-Ended Poly(ethylene glycol)"; Macromolecules; Jul. 31, 2001; pp. 6409-6419; vol. 34; American Chemical Society.
(Continued)

*Primary Examiner* — Brian Gulledge
(74) *Attorney, Agent, or Firm* — Andrew D. Fortney; Central California IP Group, P.C.

(57) ABSTRACT

A block copolymer of the formula $R_f$-PEG-PAA is disclosed, where $R_f$ comprises a perfluoroalkyl group having at least 3 carbon atoms, bound to an ether oxygen atom directly or through a substituted or unsubstituted alkylene group, PEG is a poly(alkylene glycol) unit having a weight average molecular weight or number average molecular weight of from 1 to 20 kDa, and PAA is one or more poly([meth]acrylic acid) units having a total weight average molecular weight or number average molecular weight of from 0.3 to 10 kDa. A polymer mixture including the block copolymer, a co-hydrogel and a drug delivery vehicle including the polymer mixture, and methods of synthesizing the block copolymer, forming a sol-gel two-phase co-hydrogel, forming a drug delivery vehicle, and delivering a drug to a patient in need thereof are also disclosed.

17 Claims, 25 Drawing Sheets

(51) Int. Cl.

| | |
|---|---|
| C08L 33/02 | (2006.01) |
| C08J 3/075 | (2006.01) |
| A61K 9/06 | (2006.01) |
| A61K 9/00 | (2006.01) |
| C08F 297/02 | (2006.01) |
| C08G 65/48 | (2006.01) |
| C08G 18/28 | (2006.01) |
| C08G 81/02 | (2006.01) |
| C08L 71/02 | (2006.01) |
| C08F 293/00 | (2006.01) |
| C08G 18/48 | (2006.01) |
| C08G 18/75 | (2006.01) |
| A61K 47/34 | (2017.01) |
| C08G 83/00 | (2006.01) |

(52) U.S. Cl.
CPC ...... *C08F 297/026* (2013.01); *C08G 18/2885* (2013.01); *C08G 18/4833* (2013.01); *C08G 18/755* (2013.01); *C08G 65/48* (2013.01); *C08G 81/025* (2013.01); *C08J 3/075* (2013.01); *C08L 33/02* (2013.01); *C08L 71/02* (2013.01); *C08L 101/04* (2013.01); *A61K 47/34* (2013.01); *C08F 2438/03* (2013.01); *C08G 83/008* (2013.01); *C08G 2210/00* (2013.01); *C08J 2333/02* (2013.01); *C08J 2371/02* (2013.01); *C08J 2400/102* (2013.01); *C08J 2451/08* (2013.01); *C08L 2203/02* (2013.01)

(56) References Cited

OTHER PUBLICATIONS

Giyoong Tae et al.; "Ordering Transitions of Fluoroalkyl-Ended Poly(ethylene glycol); Rheology and SANS"; Macromolecules; Apr. 27, 2002; pp. 4448-4457; vol. 35; American Chemical Society.
Anil K. Singla et al.; "Potential Applications of Carbomer in Oral Mucoadhesive Controlled Drug Delivery System: A Review"; Drug Development and Industrial Pharmacy; 2000; pp. 913-924; vol. 26(9); Marcel Dekker, Inc.
Alka Ahuja et al.; "Mucoadhesive Drug Delivery Systems"; Drug Development and Industrial Pharmacy; 1997; pp. 489-515; vol. 23(5); Marcel Dekker, Inc.
R.J. Young et al.; "Radical Polymerization"; Introduction to Polymers, Third Edition; 2011; pp. 108-109; CRC Press.
J. Loiseau et al.; "Synthesis and Characterization of Poly(acrylic acid) Produced by RAFT Polymerization. Application as a Very Efficient Dispersant of CaCO3, Kaolin, and TiO2"; Macromolecules; Apr. 2, 2003; pp. 3066-3077; vol. 36; American Chemical Society.
M. Szwarc et al.; "Polymerization Initiated by Electron Transfer to Monomer. A New Method of Formation of Block Polymers"; Journal of American Chemical Society; 1956; pp. 2656-2657; vol. 78; https://pubs.acs.org.
Mitsuru Nagasawa; "Thermodynamic and Hydrodynamic Properties of Polyelectrolytes"; J. Polymer Sci.: Symposium No. 49; 1975; pp. 1-29; John Wiley & Sons, Inc.
Toshiaki Kitano et al.; "Anionic Polymerization of tert-Butyl Acrylate"; Polymer Journal; 1977; pp. 153-159; vol. 9, No. 2.
Sunil K. Varshney et al.; "Anionic Polymerization of Acrylic Monomers. 6. Synthesis, Characterization, and Modification of Poly(methyl methacrylate)—Poly(tert-butyl acrylate) Di- and Triblock Copolymers"; Macromolecules; 1991; pp. 4997-5000; vol. 24; American Chemical Society.
S. K. Varshney et al.; "Anionic Polymerization of (Meth)acrylic Monomers. 4. Effect of Lithium Salts as Ligands on the 'Living' Polymerization of Methyl Methacrylate Using Monofunctional Initiators"; Macromolecules; 1990; pp. 2618-2622; vol. 23; American Chemical Society.
J.-S. Wang et al.; "Anionic Polymerization of Acrylic Monomers. 16. Living Anionic Copolymerization of Methyl Methacrylate and tert-Butyl Acrylate as Promoted by Lithium 2-(2-Methoxyethoxy) Ethoxide"; Macromolecules; 1994; pp. 4635-4638; vol. 27; American Chemical Society.
Bernhard Neises et al.; "Simple Method for the Esterification of Carboxylic Acids"; Angew. Chem. Int. Ed. Engl.; 1978; pp. 522-524; vol. 17, No. 7.
Yanling Luo et al.; "Synthesis and Characterization of a Poly(acrylic acid)-graft-Methoxy Poly(ethylene oxide) Comblike Copolymer"; Journal of Applied Polymer Science; 2008; pp. 3286-3291; vol. 109; Wiley Periodicals, Inc.

* cited by examiner

Rf-PEG-Rf/Rf-PEG-PAA co-hydrogel phase

Mucus phase

Relative Maximum Detachment Force (Gram/cm$^2$)

MUCOADHESIVE AND/OR SOL-GEL CO-HYDROGEL SYSTEMS INCLUDING FLUOROALKYLATED ($R_f$) POLYETHYLENE GLYCOL (PEG) AND $R_f$-PEG-POLY(ACRYLIC ACID) (PAA) COPOLYMERS, AND METHODS OF MAKING THE SAME AND OF DRUG DELIVERY USING THE SAME

CROSS REFERENCE TO RELATED APPLICATION

This application claims the benefit of U.S. Provisional Patent Application No. 62/589,311, filed on Nov. 21, 2017, incorporated herein by reference as if fully set forth herein.

FIELD OF THE INVENTION

The present invention generally relates to the field of mucoadhesive and/or sol-gel co-hydrogel systems. More specifically, embodiments of the present invention pertain to mucoadhesive and/or sol-gel co-hydrogel systems including fluoroalkylated ($R_f$) polyethylene glycol (PEG) and $R_f$-PEG-poly(acrylic acid) (PAA) copolymers, and methods of making and using the same.

DISCUSSION OF THE BACKGROUND

Mucus is a complex, viscous, and adherent secretion that lines all body cavities exposed to the external environment. Mucus contains salts, surfactants (e.g., fatty acids, phospholipids, and cholesterol), and proteins, though 95% of it is water. The main component that is responsible for its viscoelastic gel-like properties are mucins, which are a class of high molecular weight (from 0.5 to 20 MDa) glycoproteins. Mucus provides a medium for localized drug delivery through mucoadhesive materials. Drug delivery vehicles that are localized in and retained by mucus can be used to efficiently target specific tissues to achieve systemic delivery over a long period of time to enhance the bioavailability of drugs.

Polymeric hydrogel materials with mucoadhesive properties are particularly interesting for controlled drug release to the surface of a specific mucosal tissue. Acrylic-based polymers have been extensively used for mucoadhesive applications because they exhibit very high adhesive bond strengths when in contact with mucosal tissues. In addition, these polymers exhibit pH responses. In acidic media, an acrylic-based copolymer is neutrally charged, and possesses intermolecular hydrogen bonding interaction, whereas in a basic environment, the PAA groups ionize to be negatively charged, which results in repulsion of the PAA chains from each other.

In parallel with the development of mucoadhesive polymers, progress has been made in hydrogels for sustained drug release. Of particular significance, sol-gel two-phase coexistence has been reported for the self-assembly of poly(ethylene glycol) (PEG) that is modified at both ends with fluoroalkyl groups ($R_f$-PEG-$R_f$). It has been shown that the gel and viscoelastic properties could be adjusted by varying the PEG midblock length, the $R_f$ end group molecular weight, or both. By choosing the lengths of the hydrophilic PEG and hydrophobic $R_f$ end groups, the type and rate of the erosion of the hydrogel can be controlled. An impressive feature of this system is that the gel phase maintains an equilibrium composition during the erosion process. Erosion occurs in a predictable manner through desorption of the micelles from the sol-gel interface. PEG-based hydrogels are widely used in biomedical applications. Thus, the $R_f$-PEG-$R_f$ system is a promising template for drug delivery depot and controlled and sustained drug release.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention relate to a pH sensitive, mucoadhesive and/or sol-gel two-phase co-hydrogel system for potential drug delivery applications. The system was assembled using double-terminated fluoroalkylated poly(ethylene glycol) (abbreviated as $R_f$-PEG-$R_f$) and fluoroalkyl-terminated poly(ethylene glycol)-poly(acrylic acid) copolymers (abbreviated as $R_f$-PEG-PAA). $R_f$-PEG-$R_f$ possesses sol-gel two-phase coexistence, and surface erosion properties in an aqueous medium when appropriate molecular weights of the $R_f$ groups and the PEG chains are selected (see Tae G, Kornfield J A, Hubbell J A, Johannsmann D, Hogen-Esch T E: Hydrogels with Controlled, Surface Erosion Characteristics from Self-Assembly of Fluoroalkyl-Ended Poly(ethylene glycol). Macromolecules 2001, 34:6409-6419; and Tae G, Kornfield J A, Hubbell J A, Lal J: Ordering Transitions of Fluoroalkyl-Ended Poly(ethylene glycol): Rheology and SANS. Macromolecules 2002, 35:4448-4457, the relevant portions of each of which are incorporated herein by reference). We have introduced $R_f$-PEG-PAA as a mucoadhesion promoter to the $R_f$-PEG-$R_f$ hydrogel due to PAA's well-documented mucoadhesive property (see Singla A K, Chawla M, Singh A: Potential applications of carbomer in oral mucoadhesive controlled drug delivery system: a review. Drug Dev Ind Pharm 2000, 26:913-924; and Ahuja A, Khar R K, Ali J: Mucoadhesive drug delivery systems. Drug Dev Ind Pharm 1997, 23:489-515).

Thus, the present invention relates at least in part to a block copolymer of the formula $R_f$-PEG-PAA, where $R_f$ comprises a perfluoroalkyl group having at least 3 carbon atoms, bound to an ether oxygen atom directly or through a substituted or unsubstituted alkylene group, PEG is a poly(alkylene glycol) unit having a weight average molecular weight or number average molecular weight of from 1 to 20 kDa, and PAA is one or more poly([meth]acrylic acid) units having a total weight average molecular weight or number average molecular weight of from 0.3 to 10 kDa. In various examples, $R_f$ has the formula $(C_nF_{2n+1})(C_aH_{2a})O$—, where n is an integer of at least 4, and/or a is an integer of at least 1. For example, n may be an integer of at least 6, and a may be an integer of at least 2. In addition, n may be an integer of at most 20 and/or a may be an integer of at most 2.

In further examples, the PEG consists essentially of poly(ethylene glycol). In some embodiments, the PEG has a number average molecular weight of from 0.3 to 10 kDa (e.g., from 3 to 10 kDa), Thus, the PEG may have the formula $(-CH_2CH_2O-)_m$, where in has an average value of from 50 to 250.

In further or alternative examples, the PAA consists essentially of units of the formula $(-R^1CHCH(CO_2R^2))-_p$, where $R^1$ is H or $CH_3$, $R^2$ is H or an alkali metal or ammonium ion, and p has an average value providing the total weight average molecular weight or number average molecular weight. For example, $R^1$ may be H, $R^2$ may be H or an alkali metal ion, and/or the average value of p may be from 5 to 100. In some embodiments, the PAA has a number average molecular weight of from 0.3 to 10 kDa (e.g., from 0.5 to 3 kDa).

The present invention may further relate at least in part to a polymer mixture, comprising the above block copolymer and a second perfluoroalkyl-terminated PEG polymer. In some embodiments, the second perfluoroalkyl-terminated PEG polymer has the formula $R_f$-PEG-$R_f$, where $R_f$ and PEG are as defined herein. The block copolymer and the second perfluoroalkyl-terminated PEG polymer may be present in a ratio (e.g., by weight or mass) of from 1:99 to 25:75 (e.g., the ratio of the block copolymer to the second perfluoroalkyl-terminated PEG polymer by weight may be from 5:95 to 20:80).

In further embodiments, the present invention further relates at least in part to a co-hydrogel, comprising the present polymer mixture in an aqueous environment. In some examples, the aqueous environment consists essentially of water or an aqueous buffer.

In even further embodiments, the present invention further relates at least in part to a drug delivery vehicle comprising the present polymer mixture or co-hydrogel. The drug delivery vehicle may further include a pharmaceutically active drug.

The present invention also relates at least in part to a method of synthesizing a block copolymer, comprising polymerizing (meth)acrylic acid or a $C_1$-$C_6$ ester thereof using a trithiocarbonic acid ester to produce a poly([meth]acrylic acid) or a poly([meth]acrylate ester); and reacting the poly([meth]acrylic acid) or poly([meth]acrylate ester) with a perfluoroalkyl-terminated poly(alkylene glycol) (PEG) of the formula $R_f$-PEG-OH, where $R_f$ comprises a perfluoroalkyl group having at least 3 carbon atoms, bound to an ether oxygen atom directly or through a substituted or unsubstituted alkylene group, and the PEG has a weight average molecular weight or number average molecular weight of from 1 to 20 kDa. In some embodiments, the poly([meth]acrylic acid) or poly([meth]acrylate ester) has a total weight average molecular weight or number average molecular weight of from 0.3 to 10 kDa, and/or the poly([meth]acrylic acid) or poly([meth]acrylate ester) is poly([meth]acrylic acid). Similar to the present copolymer, $R_f$ may have the formula $(C_nF_{2n+1})(C_aH_{2a})O-$, where n is an integer of at least 4 and/or a is an integer of at least 1.

In some embodiments, the trithiocarbonic acid ester has the formula $R^3(SC(=S)S)R^4$, where $R^3$ and $R^4$ are each independently $C_1$-$C_6$ alkyl, $C_6$-$C_{10}$ aryl, $C_7$-$C_{12}$ aralkyl, or $C_6$-$C_{10}$ aryl or $C_7$-$C_{12}$ aralkyl substituted with from 1 to 3 $C_1$-$C_4$ alkyl groups. For example, $R^3$ and $R^4$ may each be $C_7$-$C_{10}$ aralkyl.

Alternatively, the method of synthesizing a block copolymer may comprise polymerizing a $C_1$-$C_6$ ester of (meth)acrylic acid using a $C_1$-$C_6$ alkyl lithium as an initiator to produce a poly([meth]acrylate ester), and reacting the poly([meth]acrylate ester) with a perfluoroalkyl-terminated poly(alkylene glycol) (PEG) of the formula $R_f$-PEG-OH, wherein $R_f$ comprises a perfluoroalkyl group having at least 3 carbon atoms, bound to an ether oxygen atom directly or through a substituted or unsubstituted alkylene group, and the PEG has a weight average molecular weight or number average molecular weight of from 1 to 20 kDa, to form a copolymer of the formula $R_f$-PEG-PAE, where PAE is the poly([meth]acrylate ester).

In some embodiments of the alternative method, the initiator may further comprise a lithium halide salt. Furthermore, the poly([meth]acrylate ester) may have a total weight average molecular weight or number average molecular weight such that the corresponding poly([meth]acrylic acid) has a total weight average molecular weight or number average molecular weight of from 0.3 to 10 kDa. In some further or other embodiments of the alternative method, the method further comprises hydrolyzing the PAE to form the block copolymer (e.g., of the formula $R_f$-PEG-PAA, where PAA is a poly([meth]acrylic acid).

In a further alternative, the method of synthesizing a block copolymer may comprise reacting a poly([meth]acrylic acid) with a perfluoroalkyl-terminated poly(alkylene glycol) of the formula $R_f$-PEG-OH to form the block copolymer, and purifying the block copolymer. $R_f$ comprises a perfluoroalkyl group having at least 3 carbon atoms, bound to an ether oxygen atom directly or through a substituted or unsubstituted alkylene group, and the PEG has a weight average molecular weight or number average molecular weight of from 1 to 20 kDa. As for other aspects of the present invention, the block copolymer may have the formula $R_f$-PEG-PAA, where PAA is the poly([meth]acrylic acid), and the PAA may have a total weight average molecular weight or number average molecular weight of from 0.3 to 10 kDa.

In some embodiments, purifying the block copolymer comprises removing excess poly([meth]acrylic acid) from the block copolymer. In other or further embodiments, the poly([meth]acrylic acid) is reacted with the $R_f$-PEG-OH using an organic amine as a catalyst and a carbodiimide as a coupling reagent.

The present invention also relates at least in part to a method of forming a sol-gel two-phase co-hydrogel, comprising combining the present polymer mixture with an aqueous environment, and annealing the polymer mixture and the aqueous environment to form the sol-gel two-phase co-hydrogel. The aqueous environment may consist essentially of water (e.g., deionized water) or an aqueous buffer.

The sol-gel two-phase co-hydrogel made by this method may have mucoadhesive properties. For example, the sol-gel two-phase co-hydrogel may have a mucoadhesion greater than that of an otherwise identical hydrogel containing an equal or equivalent weight or mass of the second perfluoroalkyl-terminated PEG polymer. In some cases, mucoadhesion of the sol-gel two-phase co-hydrogel is at least 50% greater than that of the second perfluoroalkyl-terminated PEG polymer hydrogel.

In addition, the present invention relates at least in part to a method of forming a drug delivery vehicle, comprising combining the present polymer mixture with an aqueous environment and a drug, and annealing the polymer mixture, the aqueous environment and the drug to form the drug delivery vehicle. As for other aspects of the present invention, the aqueous environment may consist essentially of water or an aqueous buffer. The drug is generally a pharmaceutically active compound that is stable in an aqueous sol-gel two-phase co-hydrogel, and the drug delivery vehicle may have mucoadhesive properties. Specifically, the drug delivery vehicle has a mucoadhesion greater than (e.g., at least 50% greater than) that of an equal or equivalent weight or mass of the second perfluoroalkyl-terminated PEG polymer.

The present invention also relates at least in part to a method of delivering a drug to a patient in need thereof, comprising forming a drug delivery vehicle by the above method of forming a drug delivery vehicle, the drug delivery vehicle including the drug, and administering a pharmaceutically effective amount of the drug to the patient by applying a corresponding amount of the drug delivery vehicle to a mucus membrane of the patient.

The $R_f$-groups of $R_f$-PEG-PAA chains may be physically associated with the $R_f$ cores of the $R_f$-PEG-$R_f$ micelles, and the PEG chains from the two components may also become entangled with each other. This association may be more favorable if the PEG block in the $R_f$-PEG-PAA is longer than the outer shell thickness of the $R_f$-PEG-$R_f$ micelle. Also, with a low molar ratio of $R_f$-PEG-PAA to $R_f$-PEG-$R_f$, the sol-gel two-phase property of the $R_f$-PEG-$R_f$ hydrogel can be retained. In addition, we presume that the gel surface-bound PEG-PAA blocks of the $R_f$-PEG-PAA chains tend to protrude into the water phase, due to PAA's extreme hydrophilicity. Furthermore, when a layer of the co-hydrogel is placed on a mucous membrane, the gel surface-bound PEG-PAA blocks and mucin in the mucus secreted by the mucous membrane may interpenetrate and interact with each other, thereby promoting mucoadhesion.

These and other advantages of the present invention will become readily apparent from the detailed description of various embodiments below.

DETAILED DESCRIPTION

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The technical proposal(s) of embodiments of the present invention will be fully and clearly described in conjunction with the drawings in the following embodiments. It will be understood that the descriptions are not intended to limit the invention to these embodiments, Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

The invention, in its various aspects, will be explained in greater detail below with regard to exemplary embodiments.

Figure 1:
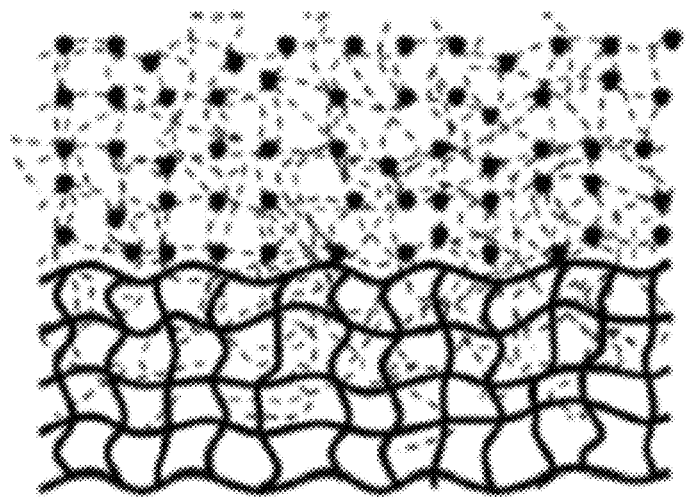
FIG. 1 shows a model of an exemplary $R_f$-PEG-$R_f$/$R_f$-PEG-PAA co-hydrogel system and illustrates chain interpenetration and interaction of the PEG-PAA blocks with mucin in the mucus layer.

FIG. 1 shows a model of the present co-hydrogel system in interaction with a mucus layer. The properties of the sol-gel two-phase coexistence and mucoadhesion of the co-hydrogel system at different pH values have been successfully tested. Drugs in any form (e.g., free drugs or drugs loaded in nanoparticles, polymers, polypeptides, proteins, or other drug delivery vehicles) can be loaded in the network of the co-hydrogel system, which can be used as controlled and sustained drug delivery depots on mucosal surfaces, including the eyes, lungs, vagina, intestine, mouth, nose, etc.

A co-hydrogel system with properties of sol-gel two-phase coexistence, pH sensitive, and mucoadhesion has been invented based on the combined properties of $R_f$-PEG-$R_f$ and acrylic-based polymers. Hydrogels based on poly (acrylic acid) (PAA) are among the most widely-accepted mucoadhesive systems, and have been widely used in topical and oral drug delivery (Singla A K, Chawla M, Singh A: Potential applications of carbomer in oral mucoadhesive controlled drug delivery system: a review. Drug Dev Ind Pharm 2000, 26:913-924; Ahuja A, Khar R K, Ali J: Mucoadhesive drug delivery systems. Drug Dev Ind Pharm 1997, 23:489-515). $R_f$-PEG-PAA copolymers have been synthesized and integrated into $R_f$-PEG-$R_f$ hydrogels. Such co-hydrogel systems possess mucoadhesion in addition to a sol-gel coexistence.

Exemplary Methods of Synthesizing Exemplary Co-Hydrogel Systems

Figure 2:
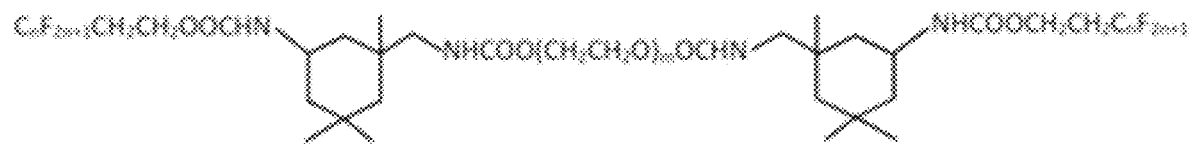
FIG. 2 shows the chemical structure of an exemplary $R_f$-PEG-$R_f$.

Synthesis of $R_f$-PEG-$R_f$ $R_f$-PEG-$R_f$ is the abbreviation for polyethylene glycol (PEG) doubly-terminated with a perfluorinated alcohol (e.g., through isophorone monourethane linking groups). 6KC6 $R_f$-PEG-$R_f$ (see FIG. 2 for the molecular structure) was made in this example, where the notation "6KC6" denotes that the molecular weight of the PEG unit is 6 kDa, and the fluorinated alcohol (having the formula $C_nF_{2n+1}CH_2CH_2$—OH) has 6 perfluorinated carbon atoms.

Figure 4A:
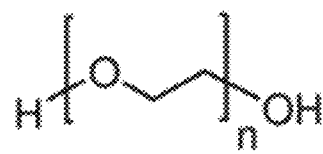
FIG. 4A shows the chemical structure of polyethylene glycol) (PEG)
Figure 4B:
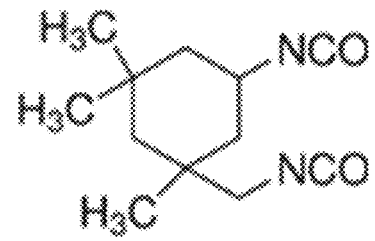
FIG. 4B shows the chemical structure of isophorone diisocyanate.

Chemicals used included poly(ethylene glycol) with an average molecular weight 6,000 Da, abbreviated as 6kPEG, the chemical structure of which is shown in FIG. 4A; 1h,1h,2h,2h-perfluorooctanol, 97% from Sigma-Aldrich, abbreviated as $C_6R_f$—OH, the chemical formula of which is $CF_3(CF_2)_5CH_2CH_2OH$ ($C_6R_f$—OH); and isophorone diisocyanate, 98% from Sigma-Aldrich, abbreviated as IPDI, the chemical structure of which is shown in FIG. 4B. The PEG (e.g., the 6kPEG) was dried by lyophilization before use. The $C_6R_f$—OH and the IPDI were vacuum distilled before use.

The $R_f$-PEG-$R_f$ synthesis procedure is briefly given herein, 1H,1H,2H,2H-perfluorooctanol (3.64 g, 0.01 mol, Mw=364.13 g/mol) and distilled isophorone diisocyanate (42 mL, density=1.061 g/ml, Mw222.28 g/mol, 0.2 mol) were put into a 100 ml 3-neck round bottom flask with a magnetic stir bar. The flask was connected to a Schlenk line and flushed with argon and/or nitrogen gas, and the reaction was stirred overnight in a 70-80° C. oil bath.

The heat and stir plate were turned off, and the 100 ml 3-neck round bottom flask was set up with a short-path distillation system (a connecting adapter, a condenser, a vacuum adapter, and a receiver). The distillation system was run under vacuum and heated. Most of the excess isophorone diisocyanate was collected at a temperature of 160° C., and an oily, dark and/or sticky intermediate appeared.

The remaining isophorone diisocyanate (IPDI) in the flask was removed by extraction with 10 ml dry hexane. More specifically, the hexane solution of the oily, dark and/or sticky intermediate was placed in a −45° C. freezer for 15 minutes to separate the intermediate from the IPDI/hexane mixture solution (e.g., by precipitation), then the supernatant was quickly decanted from the waxy residue. The hexane extraction was repeated two more times, and the intermediate was dried under vacuum overnight to get $R_f$-IPMU.

Polyethylene glycol (PEG) (1.02 g, 0.00017 mol) of nominal molecular weight 6 k was placed in a 100 ml 3-neck flask. It was dried overnight at 110° C. under vacuum. The PEG was allowed to cool and solidify under argon.

The intermediate $R_f$-IPMU (1 g, 0.0017 mol) was dissolved in 30 ml of dry ethylene glycol dimethyl ether (glyme), and this mixture was added into the 100 ml 3-neck flask under argon. The molar ratio of PEG to $R_f$-IPDU is 1:10.

The 100 ml 3-neck flask was equipped with a reflux condenser and a magnetic stir bar, and heated slowly to reflux with stirring at 70-80° C. Dibutyltin laurate (3 drops) were added to the hot solution, and the reaction was refluxed for 8 h under argon. The $R_f$-PEG-$R_f$ polymer was obtained.

After the reaction was completed, the solution was poured into 30 ml of hexane. The $R_f$-PEG-$R_f$ was subsequently separated as a white precipitate. The crude product was separated by vacuum filtration.

Another 20 ml of glyme was added to the filtrate cake, and then 20 ml hexane was added to the solution, which resulted in $R_f$-PEG-$R_f$ precipitation. The $R_f$-PEG-$R_f$ was separated by filtration again. The filtrate cake was dissolved in 15 mL of methanol, and then 20 ml diethyl ether was added to the solution to extract the polymer. The product was allowed to precipitate in the solution in the freezer overnight, then the polymer was separated by vacuum filtration. After this purification procedure was repeated two more times, the final product was dried under high vacuum overnight.

Figure 3A:
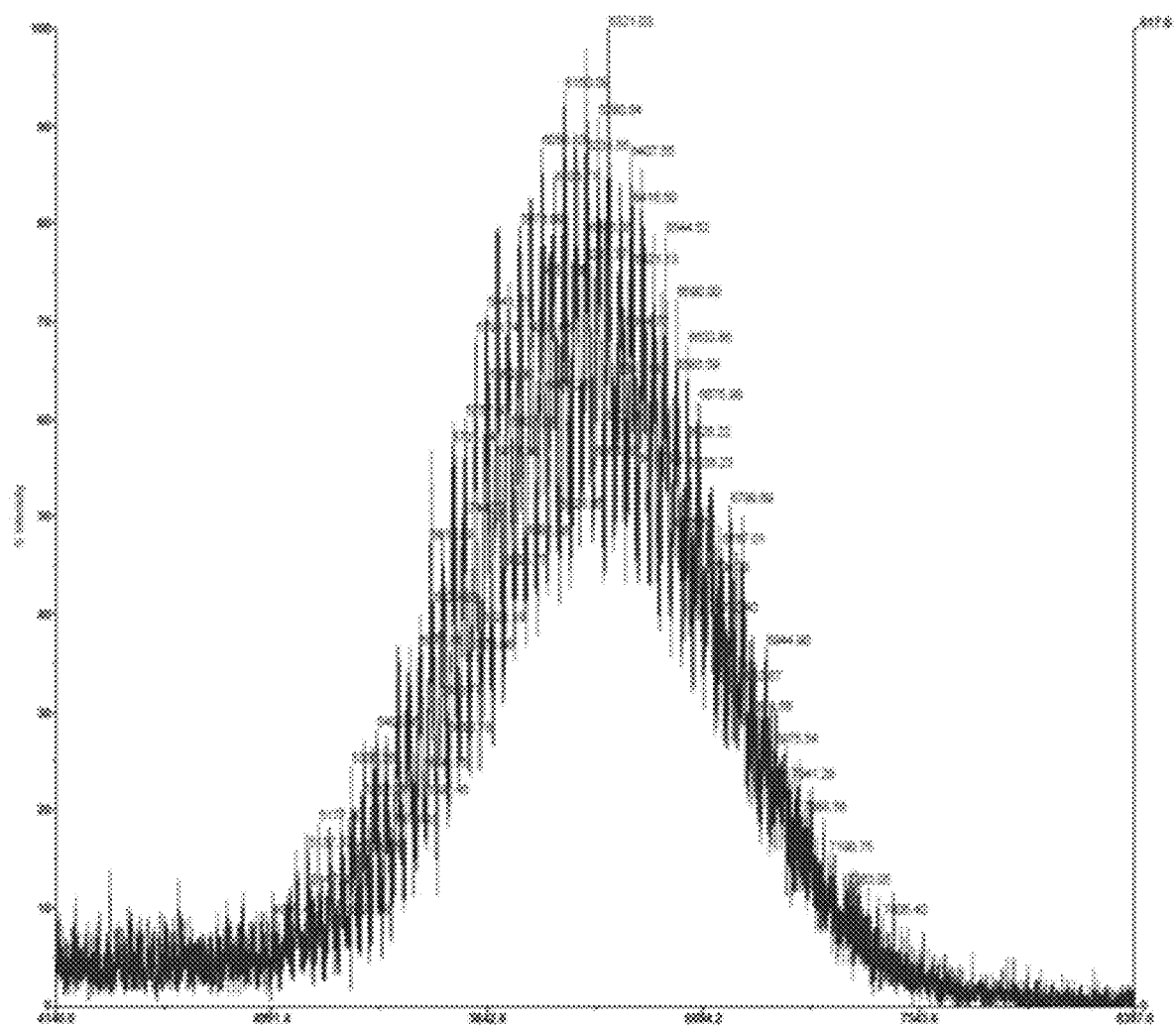
FIG. 3A shows a MALDI TOF mass spectrum of an exemplary 6 KDa PEG.
Figure 3B:
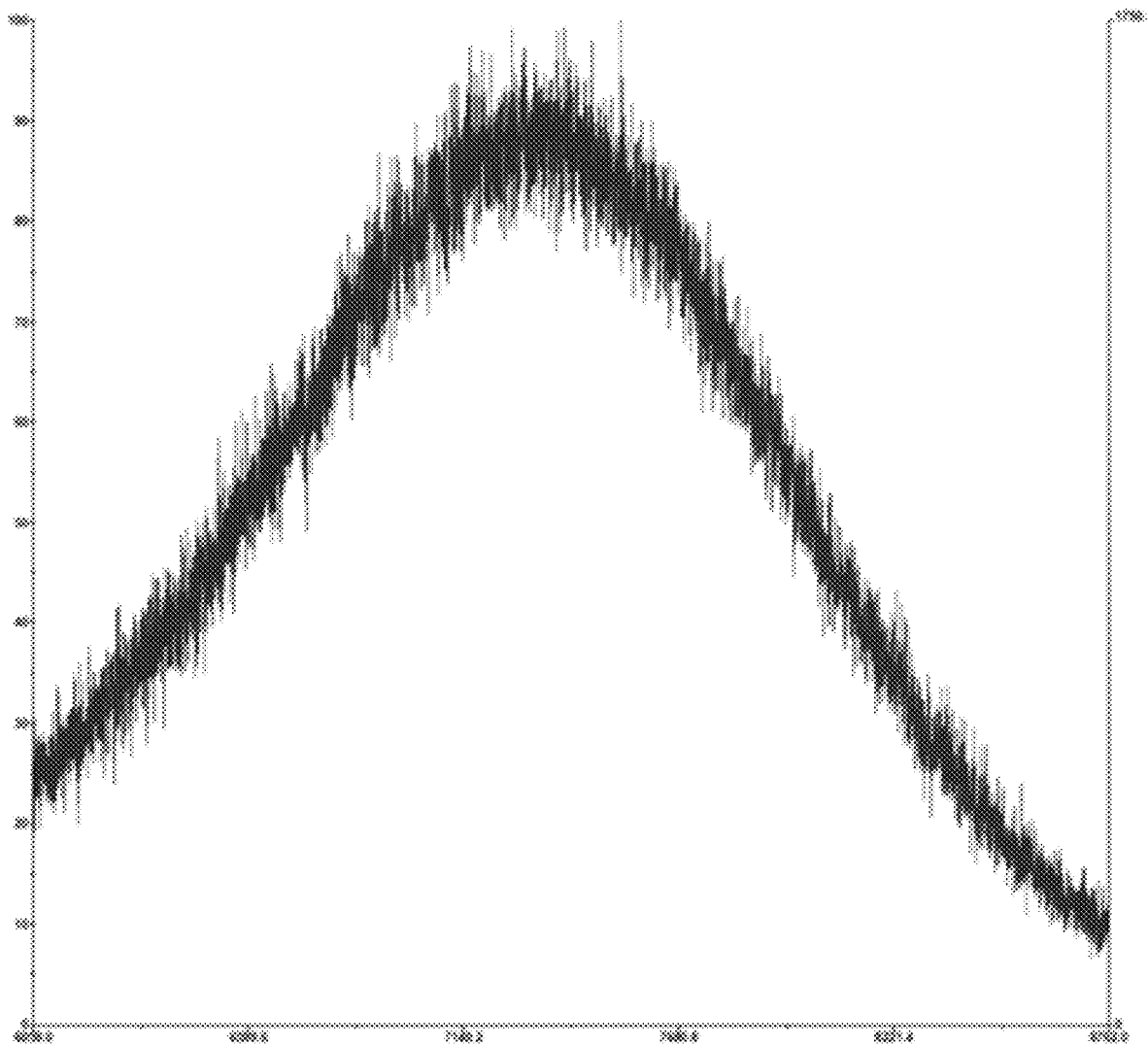
FIG. 3B shows a MALDI TOF mass spectrum of the exemplary 6KC6 $R_f$-PEG-$R_f$ in the experimental section below.

FIG. 3A shows the MALDI TOF mass spectrum of the 6 KDa PEG, and FIG. 3B shows the MALDI TOF mass spectrum of the 6 KDa $R_f$-PEG-$R_f$. The average molecular weight of the PEG is ~6.2 kDa, and that of the $R_f$-PEG-$R_f$ is 7.4 kDa, showing the success synthesis of the $R_f$-PEG-$R_f$.

Chemical Synthesis of $R_f$-PEG-OH

Figure 5:
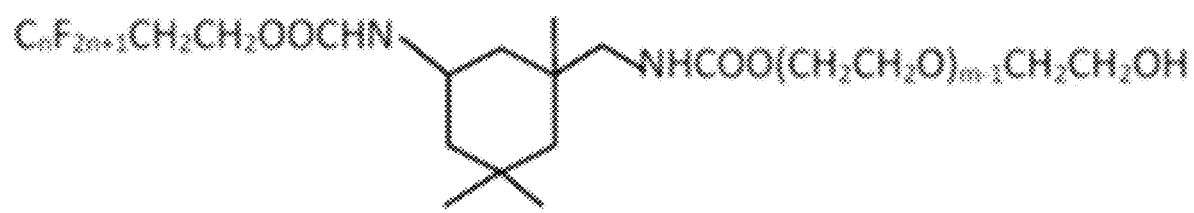
FIG. 5 shows the chemical structure of an exemplary 6KC6 $R_f$-PEG-OH.

FIG. 5 shows the chemical structure of an exemplary 6KC6 $R_f$-PEG-OH. The 6KC6 $R_f$-PEG-OH synthesis procedure is briefly given below.

Polyethylene glycol (PEG) (1.02 g, 0.00017 mol) of molecular weight 6 kDa. was placed in a 100 ml 3-neck flask. It was dried overnight at 110° C. under vacuum. The PEG was allowed to cool and solidify under argon.

The intermediate $R_f$-IPMU (0.17 g, 0.00029 mol) was dissolved in 30 ml of dry ethylene glycol dimethyl ether (glyme), and this mixture was added into the 100 ml flask under argon. The molar ratio of PEG to $R_f$-IPDU is 1:1.7.

The 100 ml 3-neck flask was equipped with a reflux condenser and a magnetic stir bar, and heated slowly to reflux with stirring at 70-80° C. Dibutyltin laurate (3 drops) were added to the hot solution, and the reaction was refluxed for 8 h under argon. An $R_f$-PEG-$R_f$ and $R_f$-PEG-OH mixture was obtained.

After the reaction was completed, the solution was poured into 30 ml of hexane. The $R_f$-PEGs were subsequently separated as a white precipitate. The crude product was separated by vacuum filtration. Another 20 ml of glyme was added to the filtrate cake, then 20 ml of hexane was added to the solution, which resulted in precipitation of the $R_f$-PEG. The $R_f$-PEG was separated by filtration. This step was then repeated one time.

The filtrate cake was dissolved in 15 mL of methanol and then 20 ml diethyl ether was added to the solution to extract the polymer. The product was allowed to precipitate from the solution in the freezer overnight, then the polymer was separated by vacuum filtration. After this purification procedure was repeated two more times, the final product ($R_f$-PEG-OH) was dried under high vacuum overnight.

Figure 6:
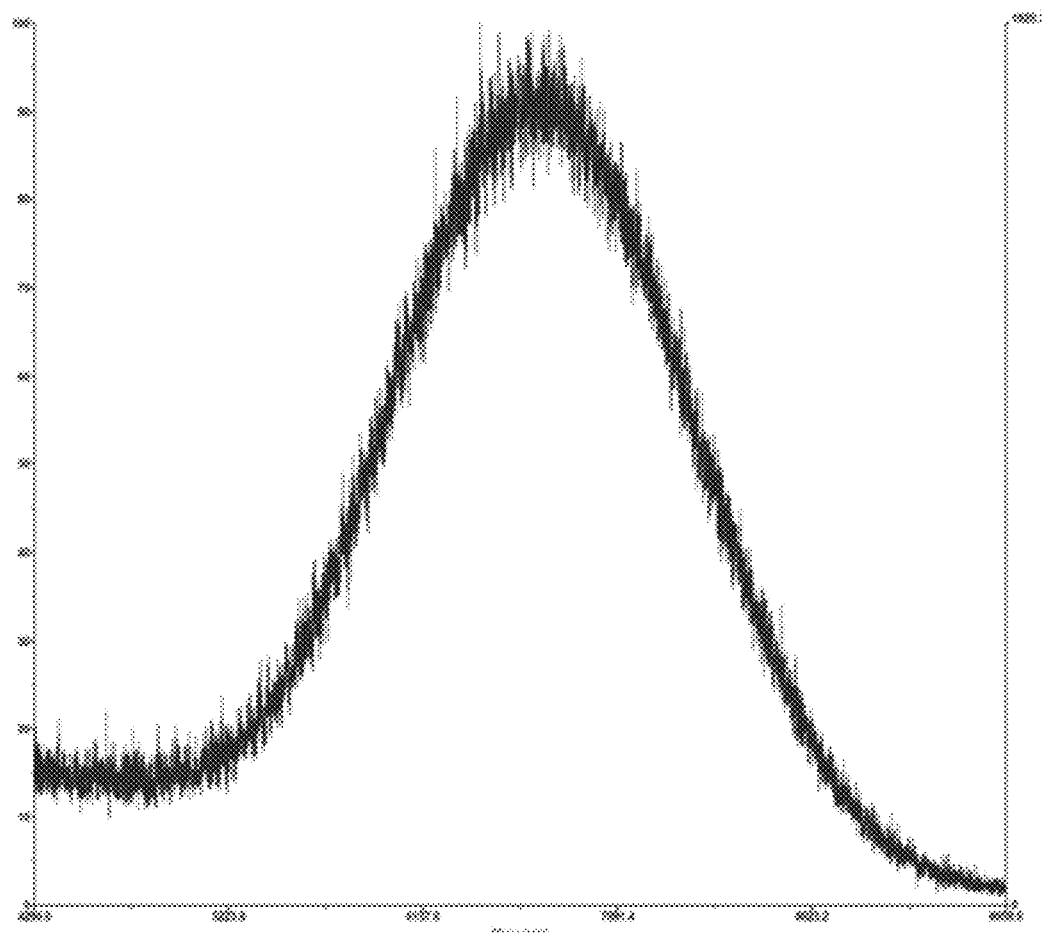
FIG. 6 shows the MALDI TOF mass spectrum of the exemplary 6KC6 $R_f$-PEG-OH in the experimental section below.

FIG. 6 shows the MALDI TOF mass spectrum of the 6KC6 $R_f$-PEG-OH. The molecular weight of this is 6.8 kDa showing the produced 6KC6 $R_f$-PEG-OH.

Figure 7:
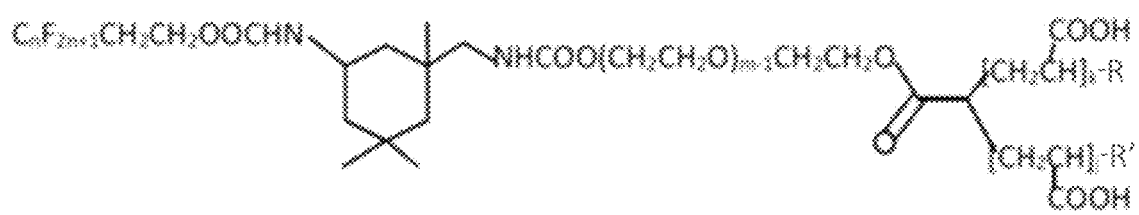
FIG. 7 is a chemical structure of an exemplary $R_f$-PEG-g-PAA.

Chemical Synthesis of $R_f$-PEG-g-PAA $R_f$-PEG-g-PAA is the abbreviation for polyacrylic acid grafted onto single-terminated perfluorooctanol isophorone monourethane polyethylene glycol. ($R_f$-PEG-g-PAA sometimes is also written as $R_f$-PEG-PAA herein.) The structure is given in FIG. 7. In FIG. 7, R and R' may independently be a $C_1$-$C_6$-alkyl group, such as methyl, t-butyl, etc., depending on how the PAA is made. The PAA was purchased from Sigma-Aldrich. The average molecular weight is listed as 1.8 kDa, but was observed to be 1.2 kDa. The $R_f$-PEG-g-PAA synthesis procedure is briefly described below.

Poly(acrylic acid) (PAA) (0.180 g, 0.1 mmol) with an average molar mass 1800 g/mol, 1-ethyl-3-(3-dimethylaminopropyl) carbodiimide hydrochloride (EDC, 0.029 g, 0.15 mmol, Mw=191.7 g/mol), and n-hydroxysuccinimide (NHS, 0.017 g, 0.15 mmol, Mw=115.09 g/mol) were dissolved in 6 mL anhydrous MT (dimethylformamide) in a 25 mL one-neck flask. This solution was stirred at room temperature overnight to form PAA-NHS ester.

Single-terminated perfluorooctanol isophorone monourethane polyethylene glycol ($R_f$-PEG-OH, 0.659 g, 0.1 mmol, Mw=6586.41 g/mol), N,N-diisopropylethylamine (DIEA, 0.0323 g, 0.25 mmol, Mw=129.24 g/mol) were added into the PAA-NHS ester solution, and the reaction was stirred for 4 days at room temperature to make $R_f$-PEG-g-PAA grafted copolymer.

The crude copolymer was mixed with a pH=7 PBS buffer in a 1:2 ratio by volume (crude product/PBS buffer=1/2) and put into a Slide-A-Lyzer 7K MWCO dialysis cassette and subjected to dialysis for 2 days. The dialysis cassette was operated at 4° C. and in PBS (pH=7) buffer solution. The purified $R_f$-PEG-g-PAA in the dialysis cassette was taken out and vacuum-dried using a lyophilizer for at least two days to yield the final product $R_f$-PEG-g-PAA.

Figure 8:
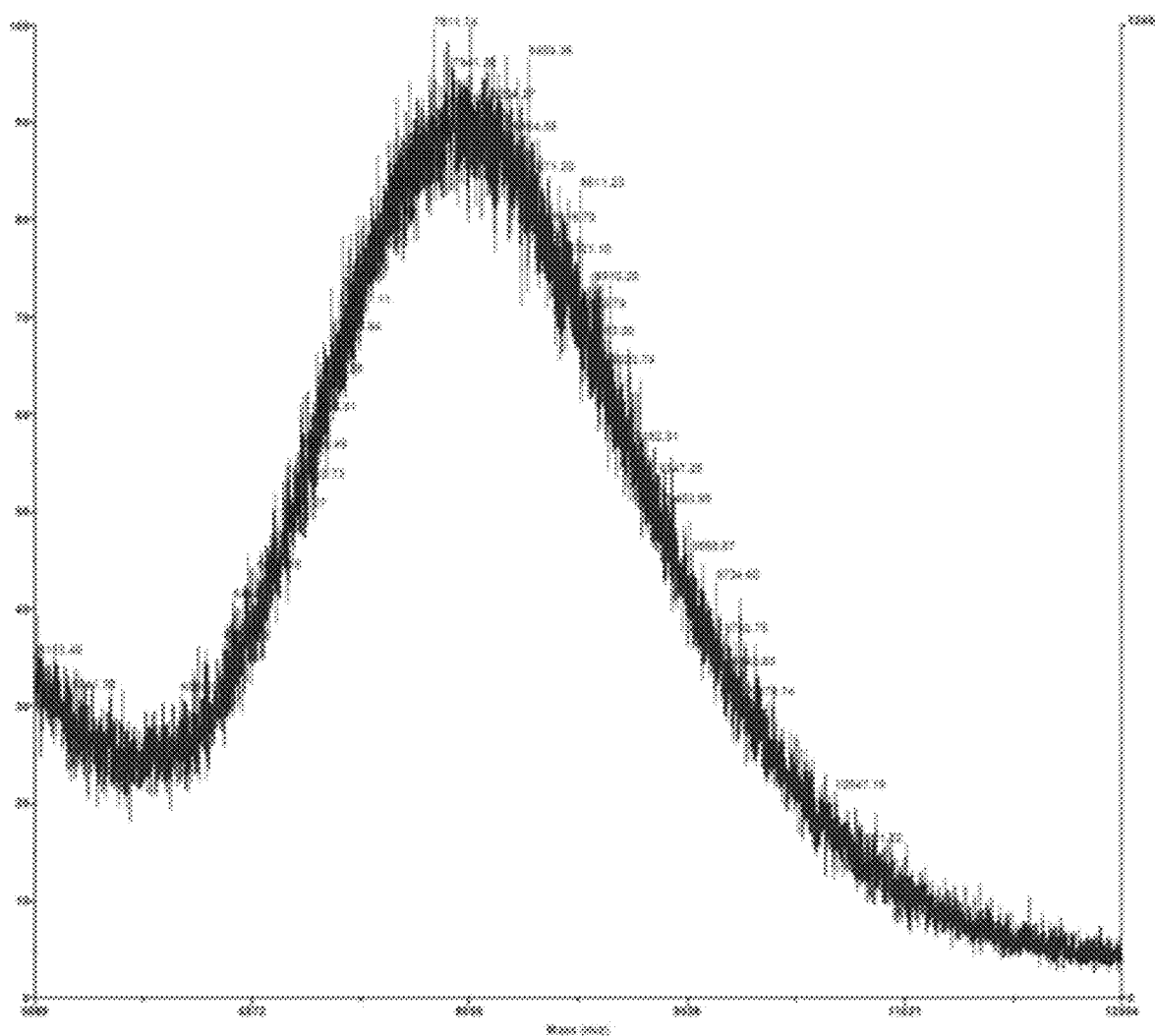
FIG. 8 is a MALDI TOF mass spectrum of an exemplary $R_f$-PEG-g-PAA in the experimental section below.

FIG. 8 shows the MALDI TOF mass spectrum of the $R_f$-PEG-g-PAA. The average molecular weight is 8.0 kDa, showing the successful synthesis of a $R_f$-PEG-g-PAA product.

Figure 9:
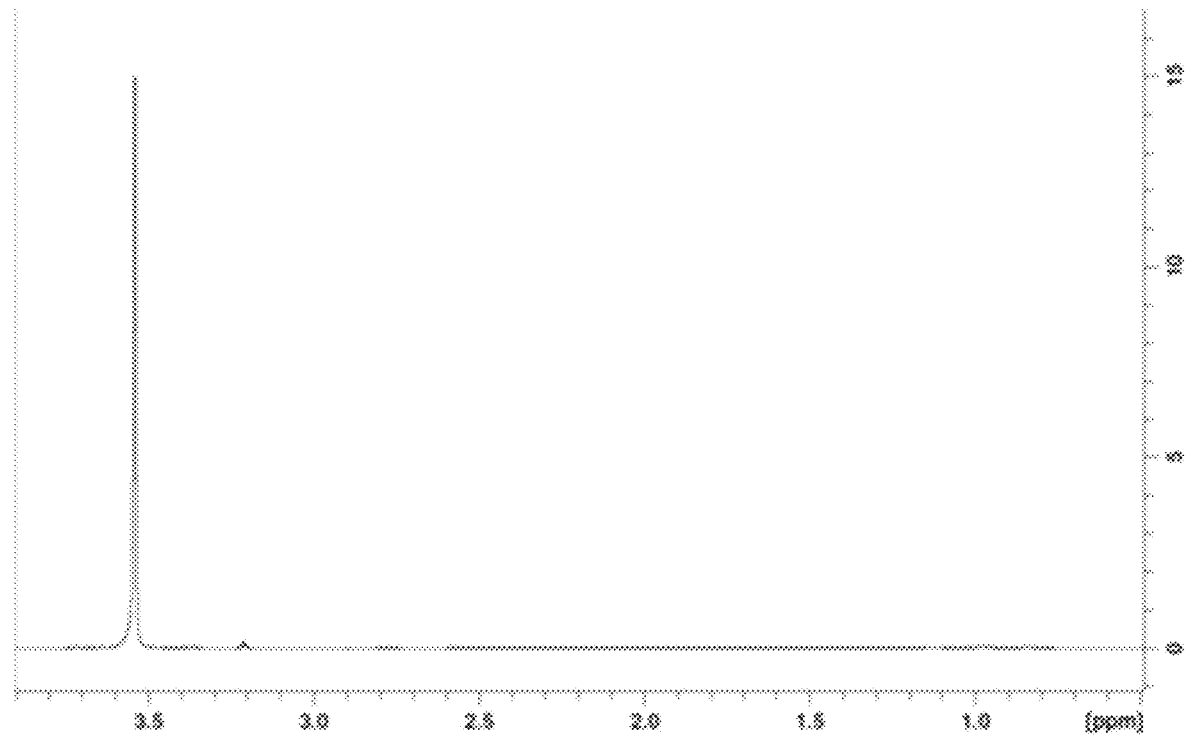
FIG. 9 is an $^1$H NMR spectrum of the $R_f$-PEG-g-PAA dissolved in deuterated methanol.
Figure 10:
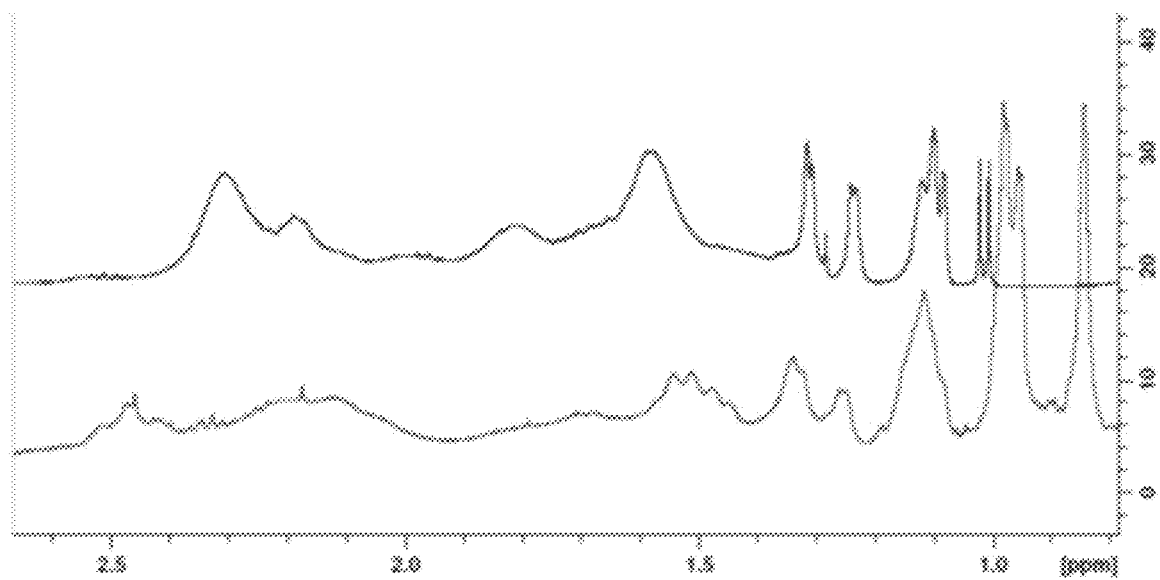
FIG. 10 is a comparison of regions of the $^1$H NMR spectra of PAA (top, blue) and $R_f$-PEG-g-PAA (bottom, red).

FIG. 9 shows the $^1$H NMR spectrum of the $R_f$-PEG-g-PAA, dissolved in deuterated methanol. The major peak at 3.5407 ppm shows the —[$CH_2CH_2O$]— groups. The PAA $^1$H signals are quite broadly distributed from 1.0 ppm to 2.5 ppm, which can only be seen clearly after the relative intensity of the spectrum is increased. FIG. 10 compares the spectra of $R_f$-PEG-g-PAA and the PAA in the PAA region. The polymers were dissolved in deuterated methanol. The top spectrum is PAA, and the bottom spectrum is the synthesized $R_f$-PEG-g-PAA. It is clear that the PAA block was transferred to the $R_f$-PEG-g-PAA copolymer, thereby demonstrating successfully synthesis of a $R_f$-PEG-g-PAA copolymer.

Preparation of Different Physical Combinations of $R_f$-PEG-$R_f$ and $R_f$-PEG-g-PAA Co-Hydrogels A 5.0% $R_f$-PEG-g-PAA/95.0% $R_f$-PEG-$R_f$ (by weight) homogeneous solid mixture was made by dissolving corresponding amounts of $R_f$-PEG-g-PAA and $R_f$-PEG-$R_f$ in methanol and then lyophilizing overnight. 320 mg of the dried 5% $R_f$-PEG-g-PAA/95% $R_f$-PEG-$R_f$ were separately mixed with 11.0 mL deionized (DI) water, 11.0 mL PBS buffer (pH=7.2), or 11.0 mL glycine/NaOH (pH=10.6) buffer. Annealing of the co-hydrogens took 7 days before use in the mucoadhesion experiments. The gel phase and sol phase were separated, and the gel phase was used to do the mucoadhesion experiment. The co-hydrogels so made form uniform gel phases. The following solutions were made using the above procedure (percentages given are by weight):
- 100.0% $R_f$-PEG-$R_f$
- 5.0% $R_f$-PEG-g-PAA/95.0% $R_f$-PEG-$R_f$
- 7.5% $R_f$-PEG-g-PAA/92.5% $R_f$-PEG-$R_f$
- 10.0% $R_f$-PEG-g-PAA/90.0% PEG-$R_f$
- 12.5% $R_f$-PEG-g-PAA/87.5% $R_f$-PEG-$R_f$
- 15.0% $R_f$-PEG-g-PAA/85.0% $R_f$-PEG-$R_f$
- 5.0% PAA/95.0% $R_f$-PEG-$R_f$ (the 5.0% PAA corresponds to the amount of PAA in the 5.0% $R_f$-PEG-g-PAA/ 95.0% $R_f$-PEG-$R_f$ the actual percentage is 0.9% PAA/ 99.1% $R_f$-PEG-$R_f$.)
- 10.0% PAA/90.0% $R_f$-PEG-$R_f$ (i.e., 1.9% PAA/98.1% $R_f$-PEG-$R_f$; see the preceding bullet point)
- 5.0% $R_f$-PEG-PAA (5.0% $R_f$-PEG-PAA corresponds to the amount of PAA in the 5.0% $R_f$-PEG-g-PAA/95.0% $R_f$-PEG-$R_f$ mixture)
- 10.0% $R_f$-PEG-PAA (see the preceding bullet point)

Note: The percentages refer to those of the polymers in the dry polymer mixtures, but not the actual polymer concentrations in the buffers. The total concentration of all polymers in each of the samples is 2.8 wt %.

Preparation of Artificial Mucus

Mucin Type II from porcine stomach was purchased from Sigma-Aldrich. 5.0 wt % mucin solution was prepared by dissolving 0.5 g mucin in 9.5 mL buffer in a 50 mL Falcon tube followed by vortexing for 15 min. Afterwards, the solution was annealed for 1 hour before use.

Experimental Procedure of the Mucoadhesion Study

A TA.XTplus texture analyzer (Stable Micro Systems, Godalming, Surrey, England) and super strong waterproof black adhesive double-sided foam mounting tape—car, trim, plate (25 mm×5 m, www.amazon.com) were used for the experiments. Exponent software from Stable Micro Systems was used for analyzing the data. The mucoadhesion of the different physical combinations of $R_f$-PEG-$R_f$ and $R_f$-PEG-g-PAA co-hydrogels described above with the porcine stomach mucin Type II were compared. Experimental conditions for the texture analyzer included the following settings:
Option: Adhesive Test
Pre-Test Speed: 0.10 mm/s
Test Speed: 0.10 mm/s
Post-Test Speed: 2.0 mm/s
Applied Force: 250.0 g
Return Distance: 11.000 mm
Contact Time: 60.00 s
Trigger Type: Auto
Trigger Force: 150.0 g
Acquisition Rate: 500 pps
Typical Test Time: 250 s The accessory was a TA-108 tortilla/film fixture with a rounded end probe. The following samples were tested:
100.0% $R_f$-PEG-$R_f$
5.0% $R_f$-PEG-g-PAA/95.0% $R_f$-PEG-$R_f$
7.5% $R_f$-PEG-g-PAA/92.5% $R_f$-PEG-$R_f$
10.0% $R_f$-PEG-g-PAA/90.0% $R_f$-PEG-$R_f$
12.5% $R_f$-PEG-g-PAA/87.5% $R_f$-PEG-$R_f$
15.0% $R_f$-PEG-g-PAA/85.0% $R_f$-PEG-$R_f$
10.0% PAA/90.0% $R_f$-PEG-$R_f$
5.0% PAA/95.0% $R_f$-PEG-$R_f$
5.0% $R_f$-PEG-PAA
10.0% $R_f$-PEG-PAA
5% Mucin Type II from porcine stomach All of the above samples were prepared in water (pH=4-5; the pKa of acrylic acid=4.25), PBS (pH=7.2), and glycine/NaOH (pH=10.6) buffers, respectively.

Figure 11:
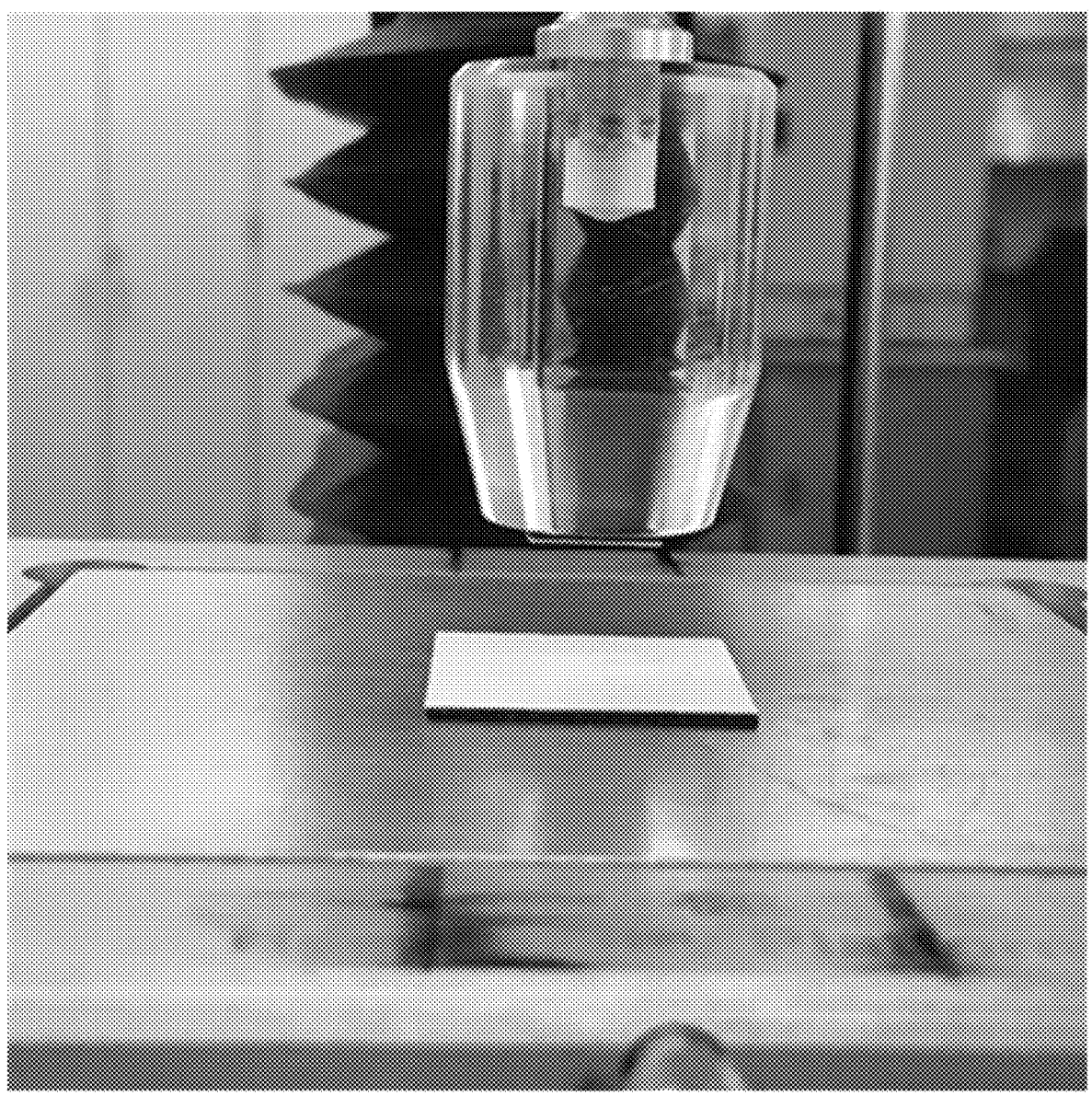
FIG. 11 is a photo of an exemplary texture analyzer in an experimental setting.

Test Set-Up:

A 25 mm×25 mm double-sided tape was placed on the center of the platform. The tape was covered with 25 mm×25 mm filter paper. Also, a 10 mm×10 mm double-sided tape was adhered to the center of the round probe. The bottom side of the tape was covered with 10 mm×10 mm filter paper (see FIG. 11.) A 30 μL sample (a-j) was applied onto the 10 mm×10 mm filter (top), and a 185 sample (k) was applied onto on the 25 mm×25 mm filter paper (bottom). The samples were annealed by waiting for 5 minutes before running each test. When the test was run, the force of the probe on the sample secured the double-sided tapes to the platform and prevented the double-sided tape from lifting as the probe was withdrawn, hence avoiding inaccuracies in the results. The adhesive test was then commenced. After each test, the probe was cleaned with acetone, and new pieces of double-sided tape were placed on the platform and the probe. Tests were repeated at least 4 times to make sure the measurements were accurate.

Results and Discussion on Mucoadhesion

Figure 12:
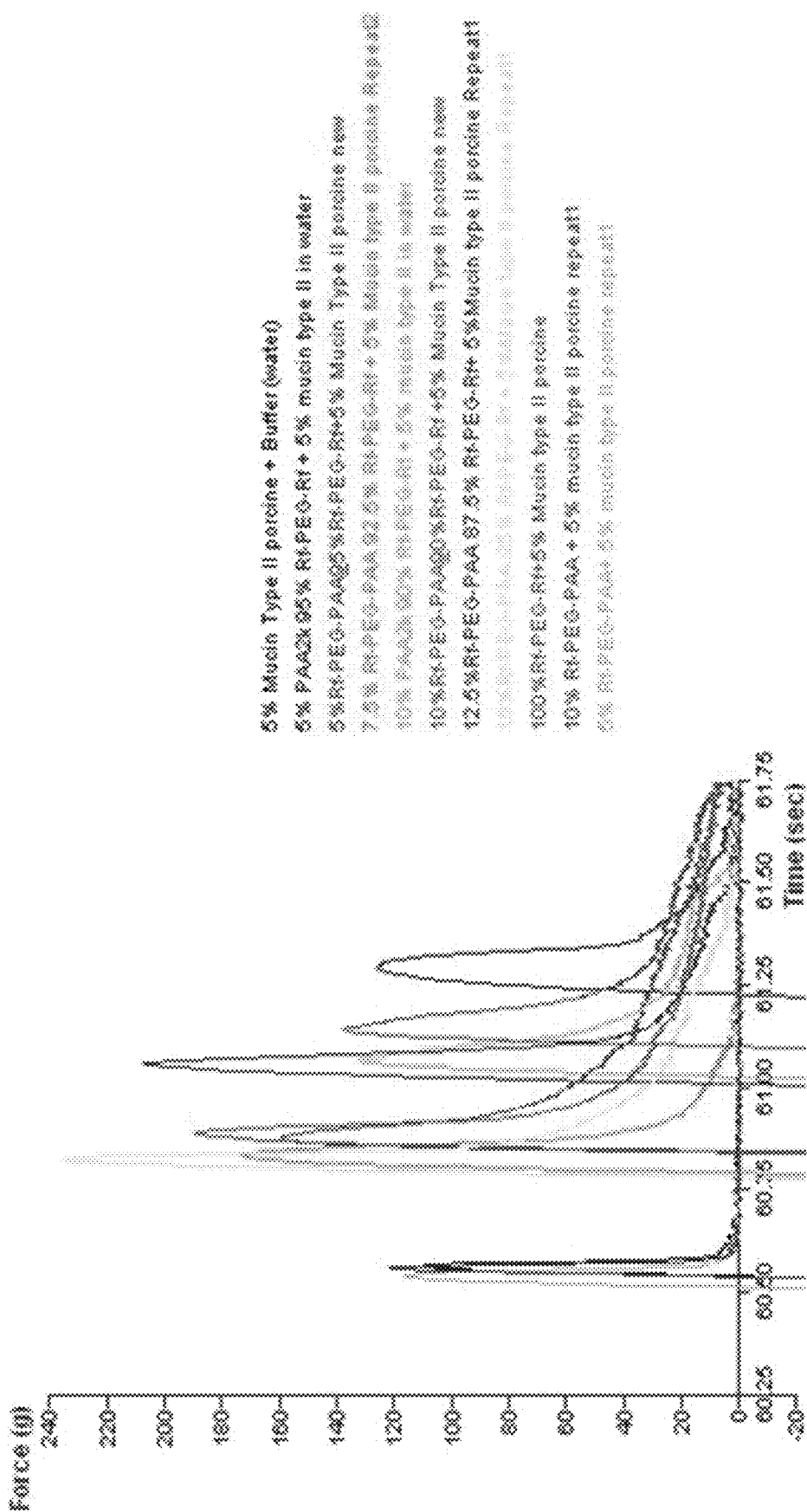
FIG. 12 shows force-vs.-time curves for a 5.0% mucin Type II solution interacting with exemplary $R_f$-PEG-$R_f$/$R_f$-PEG-g-PAA co-hydrogels in water.
Figure 13:
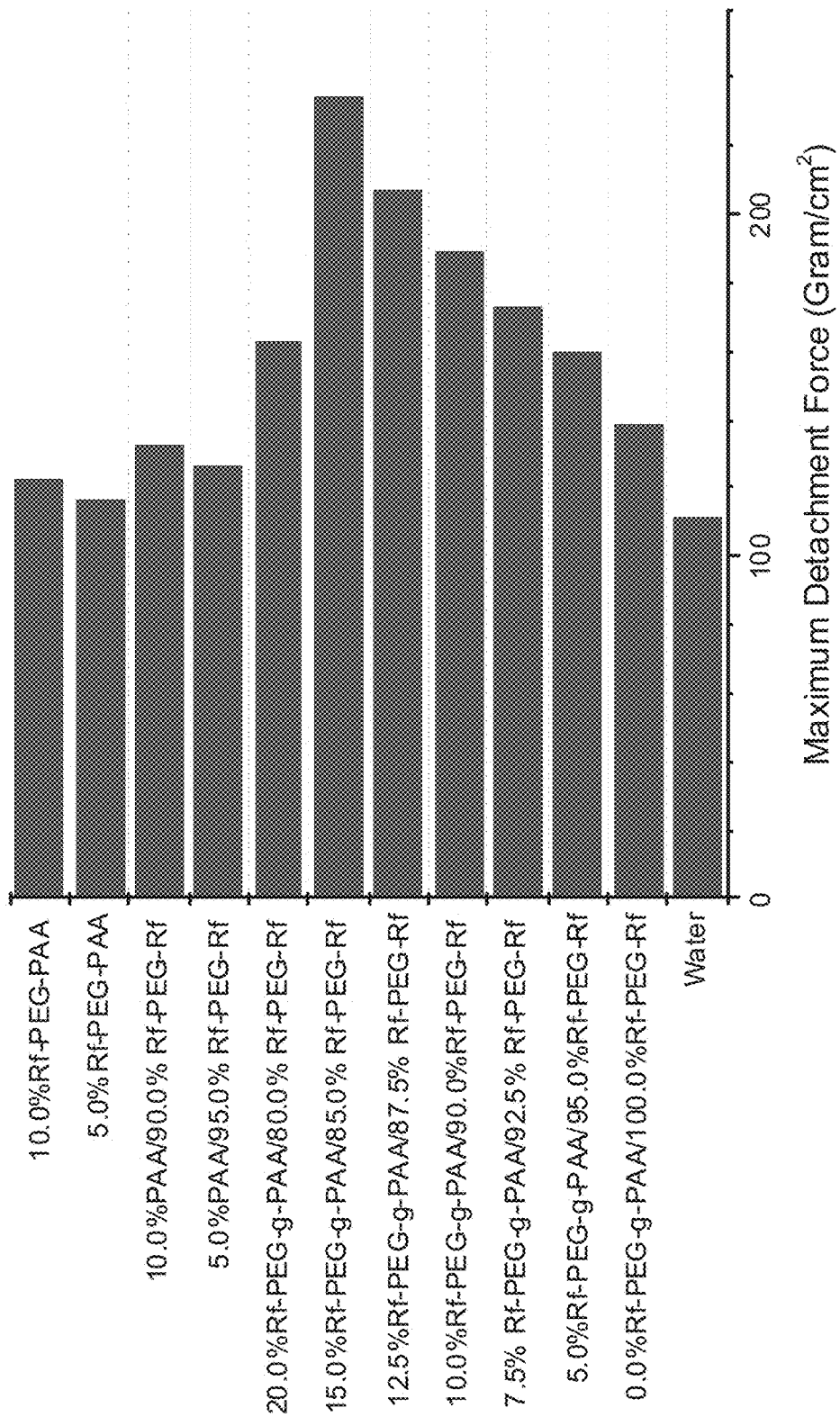
FIG. 13 is a bar graph showing the maximum detachment forces (in grams/cm$^2$) of various $R_f$-PEG-$R_f$/$R_f$-PEG-g-PAA solutions and co-hydrogels in water.

FIG. 12 shows force vs. time curves for the 5.0% mucin Type II solution interacting with the $R_f$-PEG-$R_f$/$R_f$-PEG-g-PAA co-hydrogels in water. We have observed the following. Once a trigger force of 150 g has been detected on the surface of the sample, the probe then proceeds to compress the sample until a 250 g force value was attained. The force is then held for 60 seconds to let the $R_f$-PEG-$R_f$/$R_f$-PEG-g-PAA co-hydrogels have enough contact time with the mucin solution. Then, the probe was withdrawn to a maximum distance of 11 mm above the sample. The maximum detachment forces required to separate the two surfaces were shown as the tops of the peaks. FIG. 13 shows the maximum detachment forces (in grams/cm$^2$) as a bar graph for each of the solution and/or co-hydrogel samples prepared in water.

Figure 14:
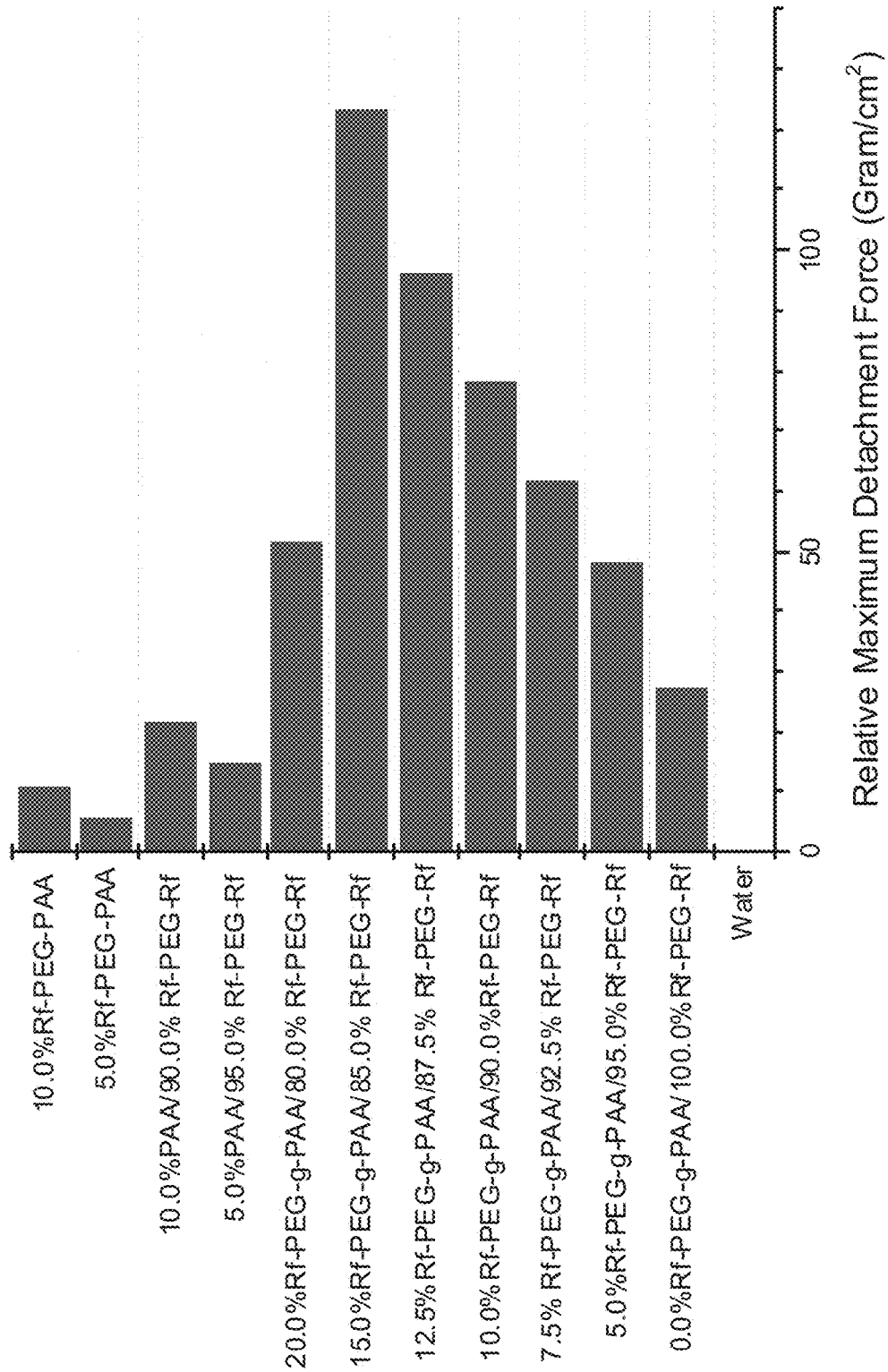
FIG. 14 is a bar graph showing relative maximum detachment forces for various $R_f$-PEG-$R_f$/$R_f$-PEG-g-PAA solutions and co-hydrogels in water.

The buffer (water) interaction with the 5.0% porcine stomach mucin Type II has the lowest MDF. This force actually shows the interaction of the wet filter paper with the mucus layer placed on the other filter paper. When this force is used as the baseline or zero reference for all of the other samples, the corrected forces (relative MDFs) are shown in FIG. 14 (which shows the relative maximum detachment forces as bar lengths for the given solutions and/or co-hydrogels prepared in water).

The 0.0% $R_f$-PEG-PAA/100.0% $R_f$-PEG-$R_f$ interacting with the 5.0% porcine stomach mucin type II has a relative MDF of 27.058 g/cm$^2$. The 5.0% $R_f$-PEG-PAA/95.0% $R_f$-PEG-$R_f$ interacting with the 5.0% porcine stomach mucin type II has a relative MDF of 48.062 g/cm$^2$. Thus, the relative MDF increased with the increase of the $R_f$-PEG-PAA concentration. The 15.0% $R_f$-PEG-PAA/85.0% $R_f$-PEG-$R_f$ interacting with the 5.0% porcine stomach mucin type II has a relative MDF of 123.331 g/cm$^2$. However, when the concentration is at 20.0% $R_f$-PEG-PAA/80.0% $R_f$-PEG-$R_f$, the relative MDF decreased to 51.569 g/cm$^2$. This sample lost its gel property, and was actually a solution of the mixed polymers. This observation proves that with a low molar ratio of $R_f$-PEG-PAA to $R_f$-PEG-$R_f$, the sol-gel two-phase property of the $R_f$-PEG-$R_f$ hydrogel can be retained, and that the gel surface-bound. PEG-PAA blocks in the $R_f$-PEG-PAA chains tend to protrude into the water phase, due to the extreme hydrophilicity of PAA.

To see if the $R_f$-group and the PEG chain in the $R_f$-PEG-PAA truly played a role in holding the $R_f$-PEG-PAA in the surface of the co-hydrogel, we performed experiments using the 5.0% PAA/95.0% $R_f$-PEG-$R_f$ and the 10.0% PAA/90.0% $R_f$-PEG-$R_f$. As shown in FIG. 14, the relative MDFs of the PAA/$R_f$-PEG-$R_f$ mixtures are 14.892 g/cm$^2$ and 21.193 g/cm$^2$, respectively, which are indeed much smaller than those of the 5.0% $R_f$-PEG-PAA/95.0% $R_f$-PEG-$R_f$ and 10.0% $R_f$-PEG-PAA/90.0% $R_f$-PEG-$R_f$, respectively. These results demonstrate that the $R_f$-groups and PEG chains of $R_f$-PEG-PAA polymers are physically associated with the $R_f$-cores and PEG chains of the $R_f$-PEG-$R_f$ micelles, which is even more favorable if the PEG block is longer than the outer shell thickness of the $R_f$-PEG-$R_f$ micelle.

For comparison, we also did experiments for the 5.0% $R_f$-PEG-PAA+5% porcine stomach mucin type II and the 10.0% $R_f$-PEG-PAA+5% porcine stomach mucin type II samples. As shown in FIG. 14, their relative MDFs are 5.436 g/cm$^2$ and 10.67 g/cm$^2$, which are much smaller than those of the 5.0% $R_f$-PEG-PAA/95.0% $R_f$-PEG-$R_f$ and 10.0%

$R_f$-PEG-PAA/90.0% $R_f$-PEG-$R_f$, respectively, demonstrating that the $R_f$-PEG-PAA needs to form a co-hydrogel with the $R_f$-PEG-$R_f$ in order to have the desired mucoadhesion property.

All the above results demonstrate that when a layer of the present co-hydrogel is placed on a mucous membrane, the gel surface-bound PEG-PAA blocks and mucin in the mucus secreted by the mucous membrane will interpenetrate and interact with each other, thereby promoting mucoadhesion.

Figure 15:
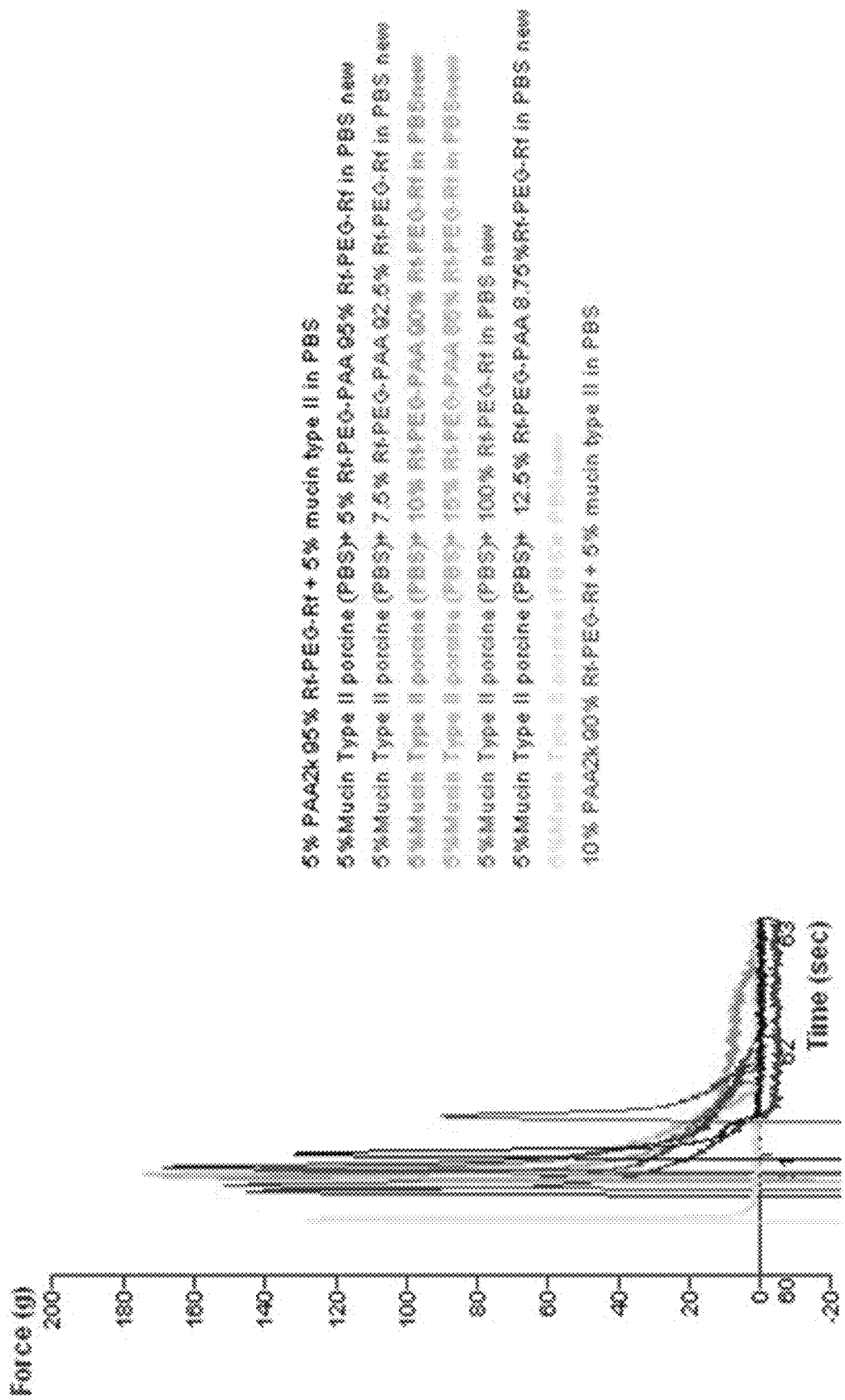
FIG. 15 shows force-vs.-time curves for a 5.0% mucin Type II solution interacting with exemplary $R_f$-PEG-$R_f$/$R_f$-PEG-g-PAA hydrogels in PBS buffer (pH=7.2).
Figure 16:
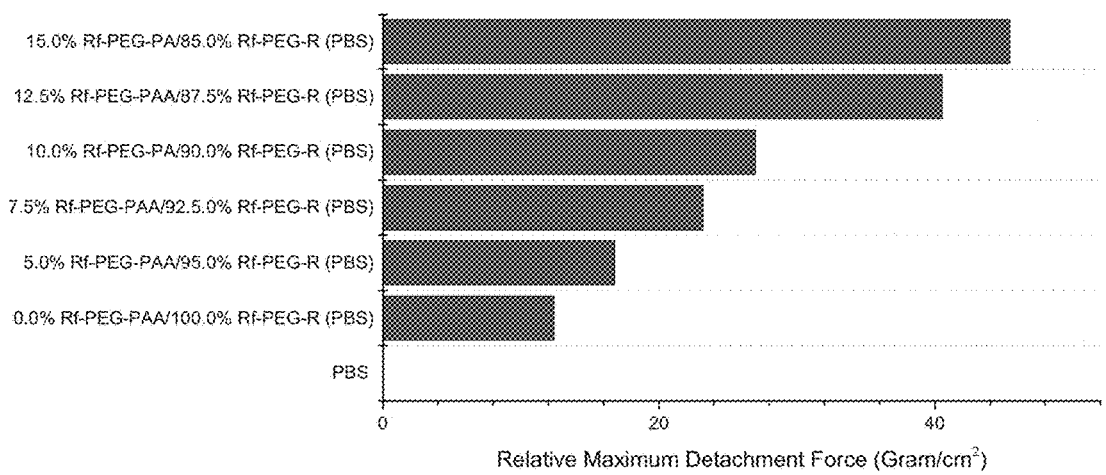
FIG. 16 is a bar graph showing relative maximum detachment forces for various $R_f$-PEG-$R_f$/$R_f$-PEG-g-PAA solutions and co-hydrogels in PBS buffer.

Results for the solution/co-hydrogel samples prepared in the PBS buffer are shown in FIGS. 15 and 16. The trend of the relative MDFs is the same as the samples prepared in water. FIG. 15 shows force vs. time curves for 5% mucin Type II interacting with the $R_f$-PEG-$R_f$/$R_f$-PEG-g-PAA hydrogels in PBS buffer (pH=7.2). FIG. 16 shows the relative maximum detachment forces as bar lengths for the given solution and/or co-hydrogel samples prepared in PBS buffer.

Figure 18:
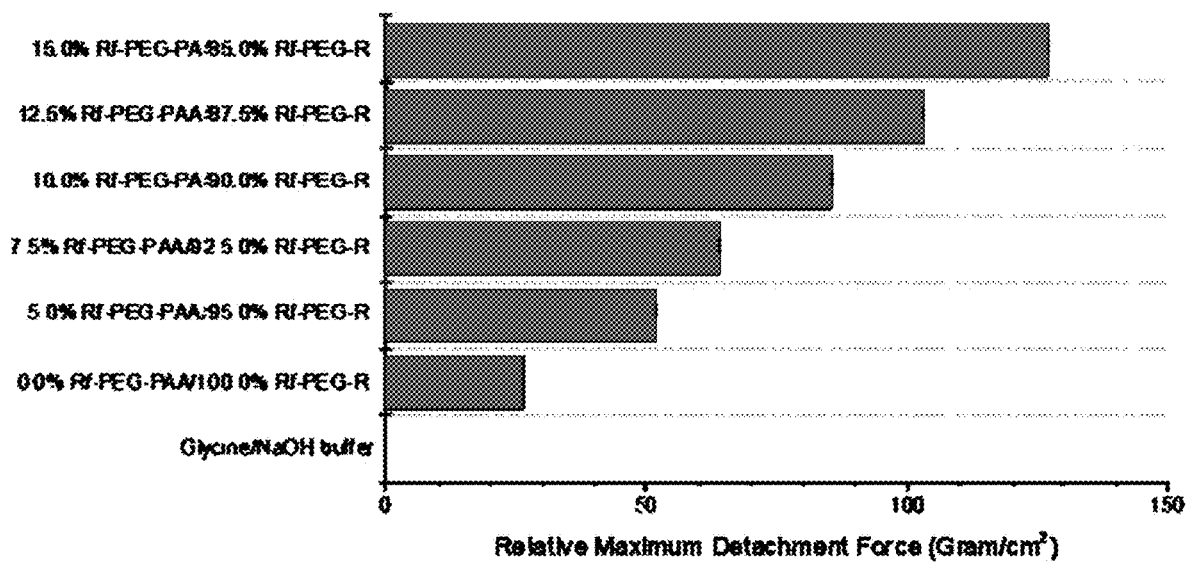
FIG. 18 is a bar graph showing relative maximum detachment forces (MDFs) for various $R_f$-PEG-$R_f$/$R_f$-PEG-g-PAA solutions and co-hydrogels in a glycine/NaOH buffer.
Figure 17:
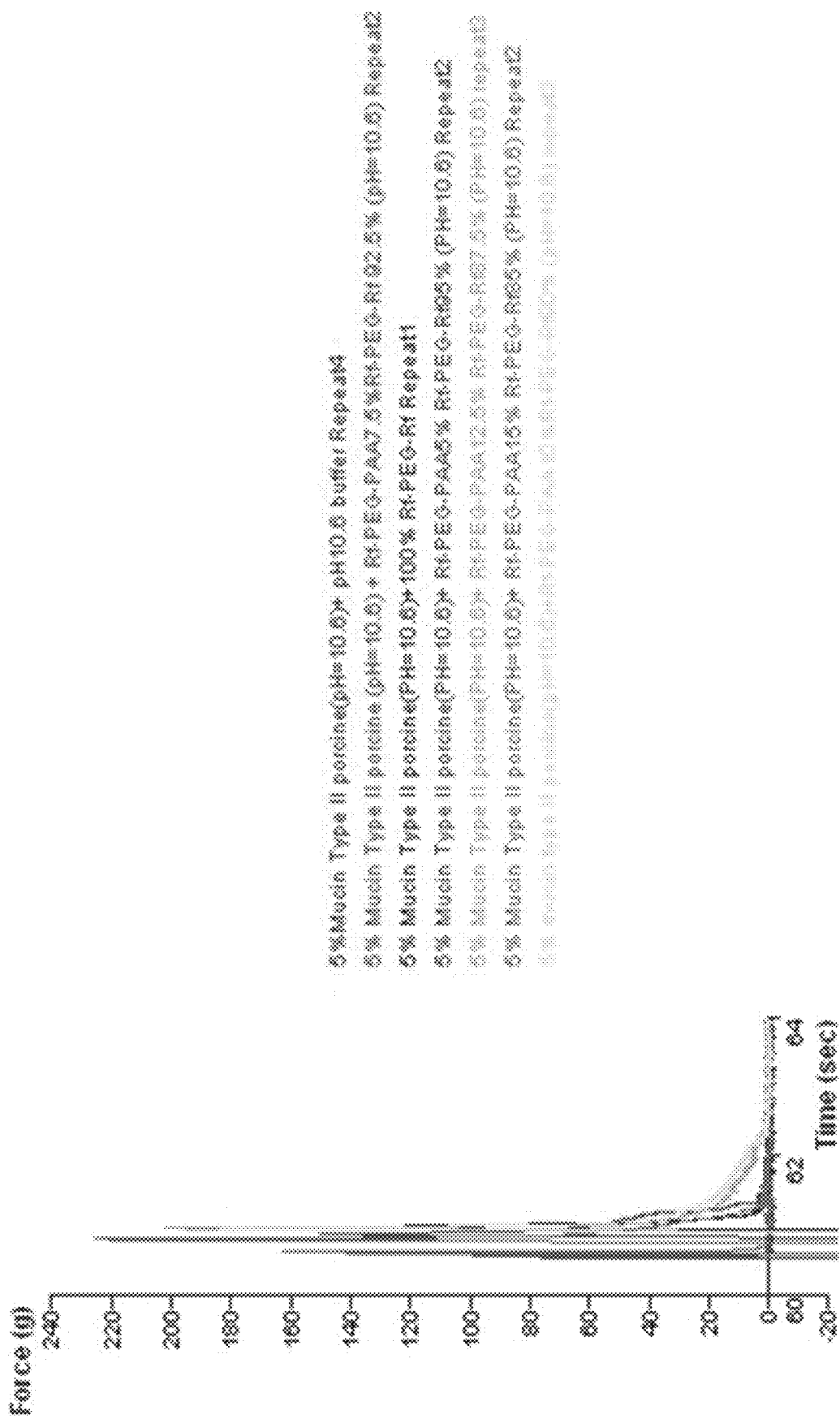
FIG. 17 shows force-vs.-time curves for a 5.0% mucin Type II solution interacting with exemplary $R_f$-PEG-$R_f$/$R_f$-PEG-g-PAA hydrogels in a glycine/NaOH buffer (pH=10.6).

Results for the samples prepared in the glycine/NaOH buffer are shown in FIGS. 17 and 18. The trend of the relative MDFs is the same as the samples prepared in water and in the PBS buffer. FIG. 17 shows force vs. time curves for 5% mucin Type II interacting with various $R_f$-PEG-$R_f$/$R_f$-PEG-g-PAA hydrogels in the glycine/NaOH buffer (pH=10.6). FIG. 18 shows the relative maximum detachment forces as bar lengths for the given solution and/or co-hydrogel samples prepared in glycine/NaOH buffer.

Figure 19:
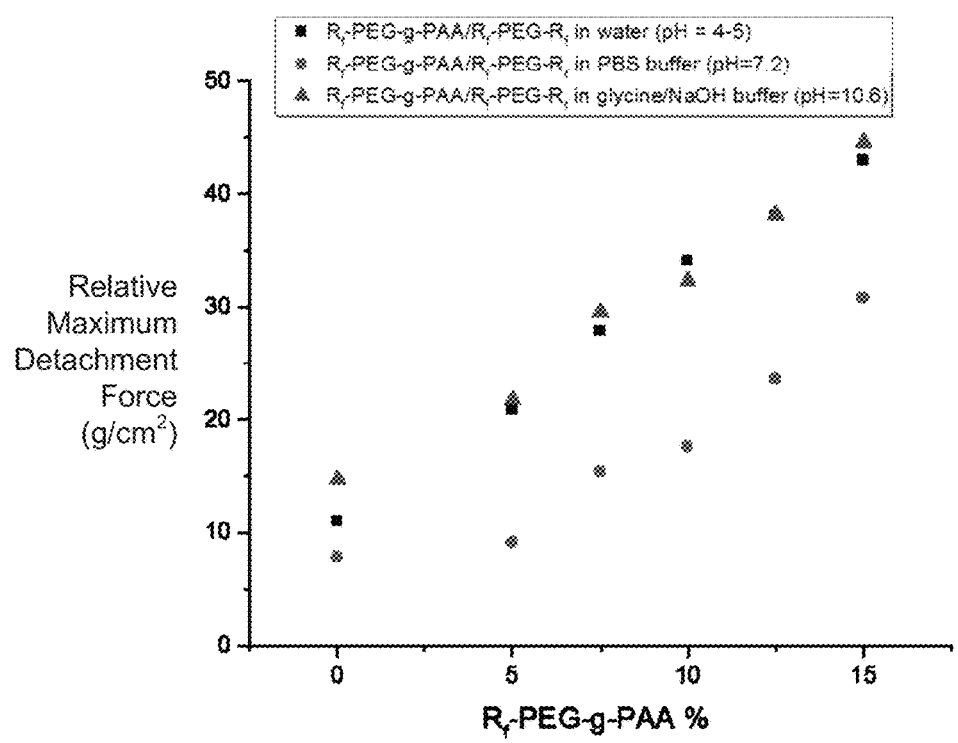
FIG. 19 is a graph comparing the MDFs of the interactions between the $R_f$-PEG-$R_f$/$R_f$-PEG-g-PAA hydrogel surfaces and the mucin solution surfaces in different buffers.

FIG. 19 shows a comparison of the relative MDFs of/in the interactions between the $R_f$-PEG-$R_f$/$R_f$-PEG-g-PAA hydrogels surfaces and the mucin solution surfaces in the different buffers. It shows that the adhesion forces of the co-hydrogels made by the glycine/NaOH buffer and water are the largest, although those made by the glycine/NaOH buffer are slightly higher, and those made by the PBS buffer are the smallest. The present co-hydrogels show pH sensitivity to/in mucoadhesion.

Mucoadhesion Studies on Pig Small Intestine

Figure 21:
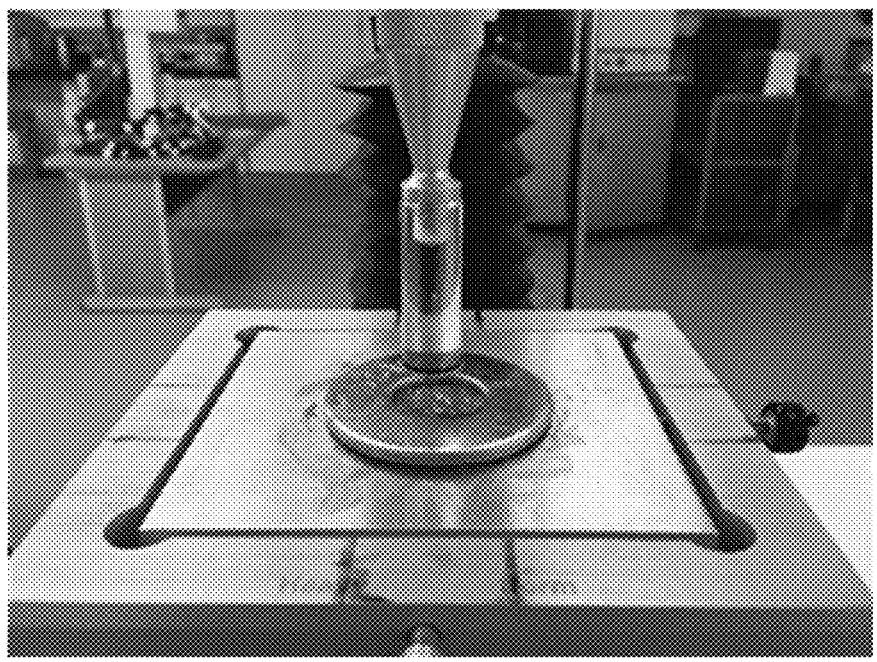
FIG. 21 shows the setting of a pig small intestine sample on the platform of a texture analyzer (TA) and a TA-10 probe above the pig small intestine sample, with a filter paper soaked with $R_f$-PEG-g-PAA and $R_f$-PEG-$R_f$ co-hydrogel glued on the bottom surface.

Instrumentation: A TA.XTplus Texture Analyzer (Stable Micro Systems, Godalming, Surrey, England) and Super Strong Waterproof Black Adhesive Double-Sided Foam Mounting Tape—Car, Trim, Plate (25 mm×5 m, purchased from www.amazon.com) were used for the experiments. Software obtained from Exponent Stable Micro Systems was used for analyzing the data. The texture analyzer settings were as follows:
Option: Adhesive Test
Pre-Test Speed: 0.10 mm/s
Test Speed: 0.10 mm/s
Post-Test Speed: 2.0 mm/s
Applied Force: 250.0 g
Return Distance: 11.000 mm
Contact Time: 60.00 s
Trigger Type: Auto
Trigger Force: 150.0 g
Acquisition Rate: 500 pps
Typical Test Time: 250 s Sample preparation: The pig small intestine was provided by BioreclamationIVT. The small intestine was rinsed with water with the mucosal surface intact. It was shipped to our lab in a frozen state. A 25 mm×25 mm sample of the pig small intestine tissue with the internal surface (the surface covered with mucosal layer) facing up was placed on the surface of the Texture Analyzer platform. A zinc-plated cut washer with an inner diameter of ¾ inch was placed on top of the small intestine sample; see FIG. 21. Double-sided tape having a diameter of 0.5 inch was adhered to the center of the TA-10 probe. The bottom side of the double-sided tape was covered with filter paper having a diameter of 0.5 inches (FIG. 21). A 0.3 mL sample (see Samples A-J below) was homogeneously applied to the filter paper. The start of each test was delayed 5 minutes to allow the homogenization of the sample on the filter paper. When the test was running, both the force of the probe and the cut washer secured the pig small intestine tissue to the platform surface. No lifting of the small intestine tissue was observed as the probe was withdrawn. After each test, the probe and the platform surface were cleaned with acetone. Then, a new sample of pig small intestine tissue and a new filter paper were placed on the analyzer platform and the end of the probe, respectively, and a new co-hydrogel was loaded onto the filter paper. Tests were repeated at least 4 times to ensure the precision and accuracy of the measurements.

In one example, a homogeneous solid mixture of 5.0% $R_f$-PEG-g-PAA/95.0% $R_f$-PEG-$R_f$ (by weight) was made by dissolving corresponding amounts of $R_f$-PEG-g-PAA and $R_f$-PEG-$R_f$ in methanol and then lyophilizing overnight. 320 mg of the dried 5% $R_f$-PEG-g-PAA/95% $R_f$-PEG-$R_f$ were separately mixed with 11.0 mL deionized (DI) water, 11.0 mL PBS buffer (pH=7.2), or 11.0 mL glycine/NaOH (pH=10.6) buffer. Annealing of the co-hydrogels took 7 days before use in the mucoadhesion experiments. The gel phase and sol phase were separated, and the gel phase was used in the mucoadhesion experiment. The co-hydrogels so made form uniform gel phases. The following solutions were made using the above procedure (percentages given are by weight):

A. 100.0% $R_f$-PEG-$R_f$
B. 5.0% $R_f$-PEG-g-PAA/95.0% $R_f$-PEG-$R_f$
C. 7.5% $R_f$-PEG-g-PAA/92.5% $R_f$-PEG-$R_f$
D. 10.0% $R_f$-PEG-g-PAA/90.0% $R_f$-PEG-$R_f$
E. 12.5% $R_f$-PEG-g-PAA/87.5% $R_f$-PEG-$R_f$
F. 15.0% $R_f$-PEG-g-PAA/85.0% $R_f$-PEG-$R_f$
G. 5.0% PAA/95.0% $R_f$-PEG-$R_f$ (the 5.0% PAA corresponds to the amount of PAA in the 5.0% $R_f$-PEG-g-PAA/95.0% $R_f$-PEG-$R_f$ mixture; the actual percentage is 0.9% PAA/99.1% $R_f$-PEG-$R_f$)
H. 10.0% PAA/90.0% $R_f$-PEG-$R_f$ (i.e., 1.9% PAA/98.1% $R_f$-PEG-$R_f$) 5.0% $R_f$-PEG-PAA (5.0% $R_f$-PEG-PAA corresponds to the amount of PAA in the 5.0% $R_f$-PEG-g-PAA/195.0% $R_f$-PEG-$R_f$ mixture)
J. 10.0% $R_f$-PEG-PAA The percentages refer to those of the polymers in the dry polymer mixtures, but not the actual polymer concentrations in the buffers. The total concentration of all polymers in each of the samples is 2.8 wt %. The mixtures of $R_f$-PEG-g-PAA and $R_f$-PEG-$R_f$ in DI water had a pH in the range of 4-5, depending on the concentration of the $R_f$-PEG-g-PAA.

Figure 23:
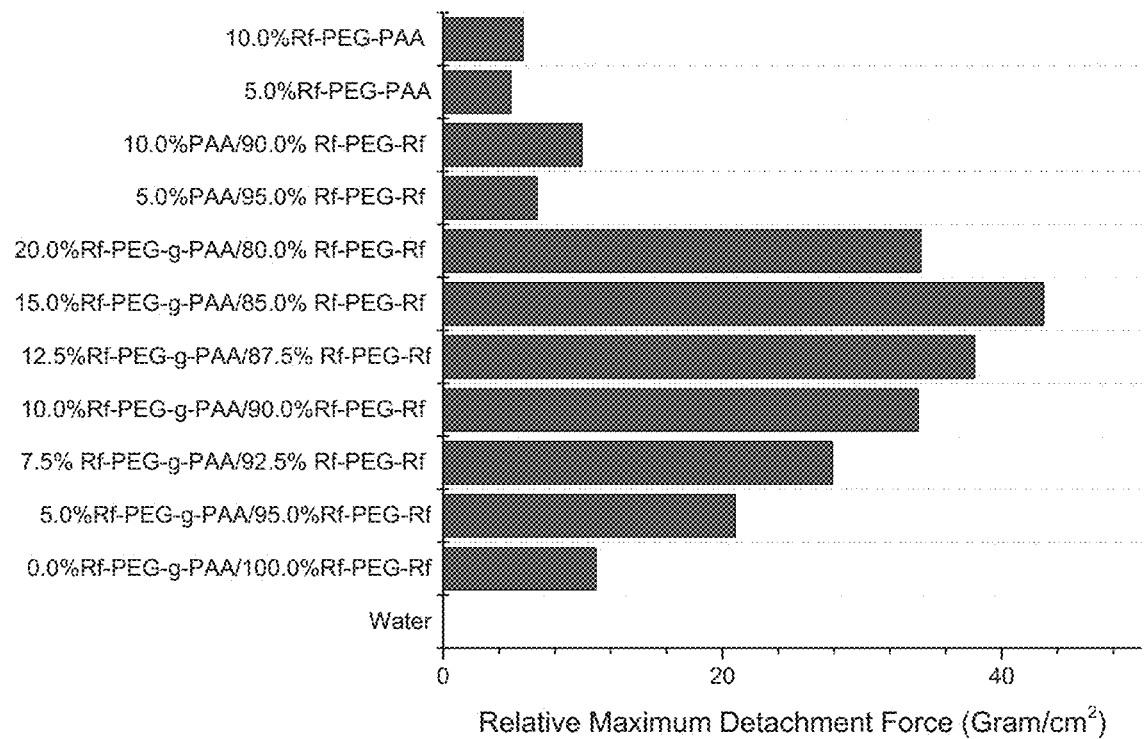
FIG. 23 is a bar graph showing relative (to water) maximum detachment forces for various $R_f$-PEG-$R_f$/$R_f$-PEG-g-PAA water solutions with pig small intestine.
Figure 22:
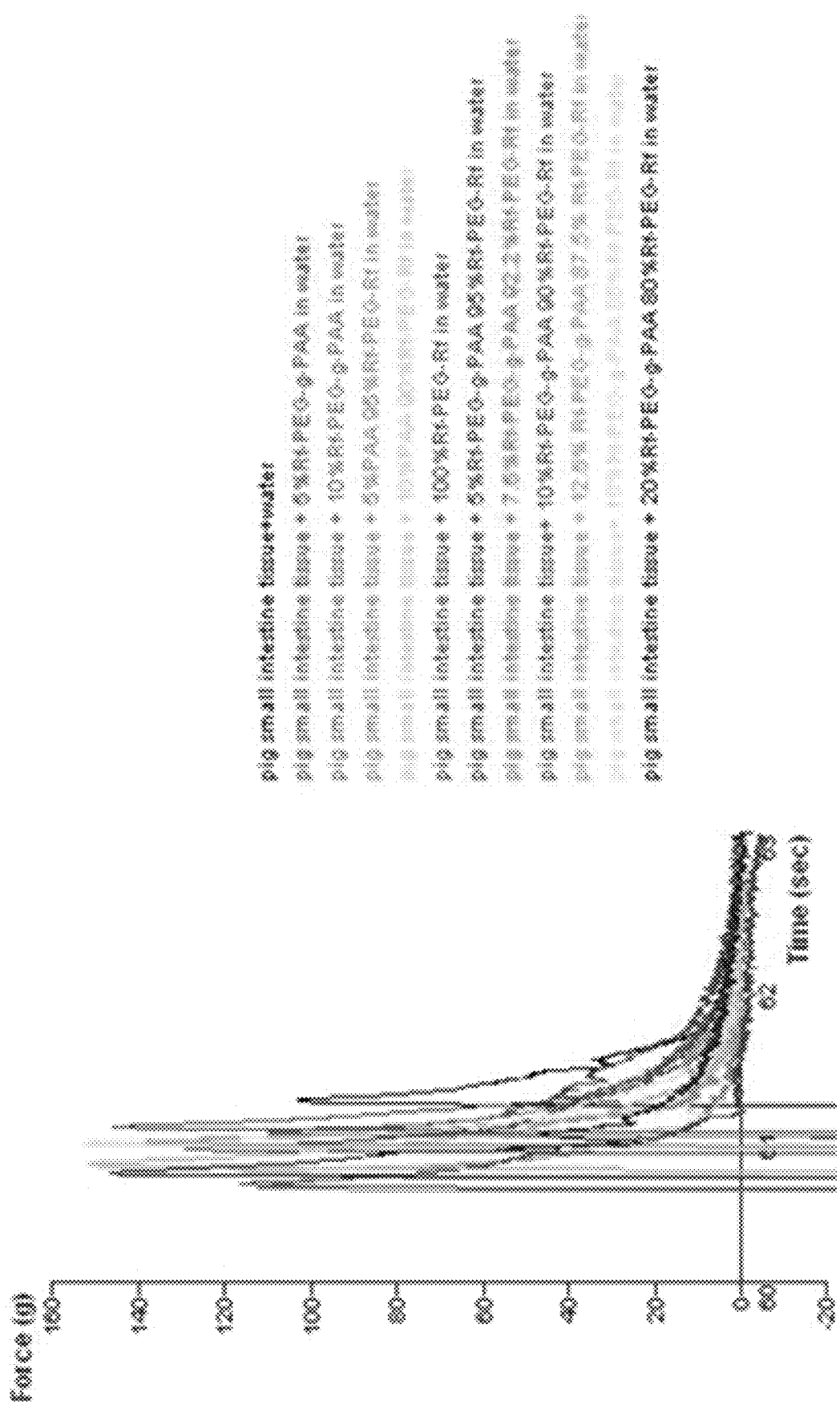
FIG. 22 shows force vs. time curves for various $R_f$-PEG-$R_f$/$R_f$-PEG-g-PAA co-hydrogels in water interacting with pig small intestine.

The results are shown in FIGS. 22 to 28. FIG. 22 shows force vs. time curves for various $R_f$-PEG-$R_f$/$R_f$-PEG-g-PAA co-hydrogels in water interacting with pig small intestine. The maximum detachment force required to separate the two surfaces are shown as the tops of the peaks. FIG. 23 is a bar graph showing maximum detachment forces (relative to water) for various $R_f$-PEG-$R_f$/$R_f$-PEG-g-PAA water solutions with pig small intestine. The $R_f$-PEG-$R_f$ hydrogel alone, the $R_f$-PEG-g-PAA hydrogel alone, and the $R_f$-PEG-$R_f$ hydrogel mixed with PAA showed a significantly lower maximum detachment force relative to the $R_f$-PEG-$R_f$/$R_f$-PEG-g-PAA co-hydrogels in water.

Figure 24:
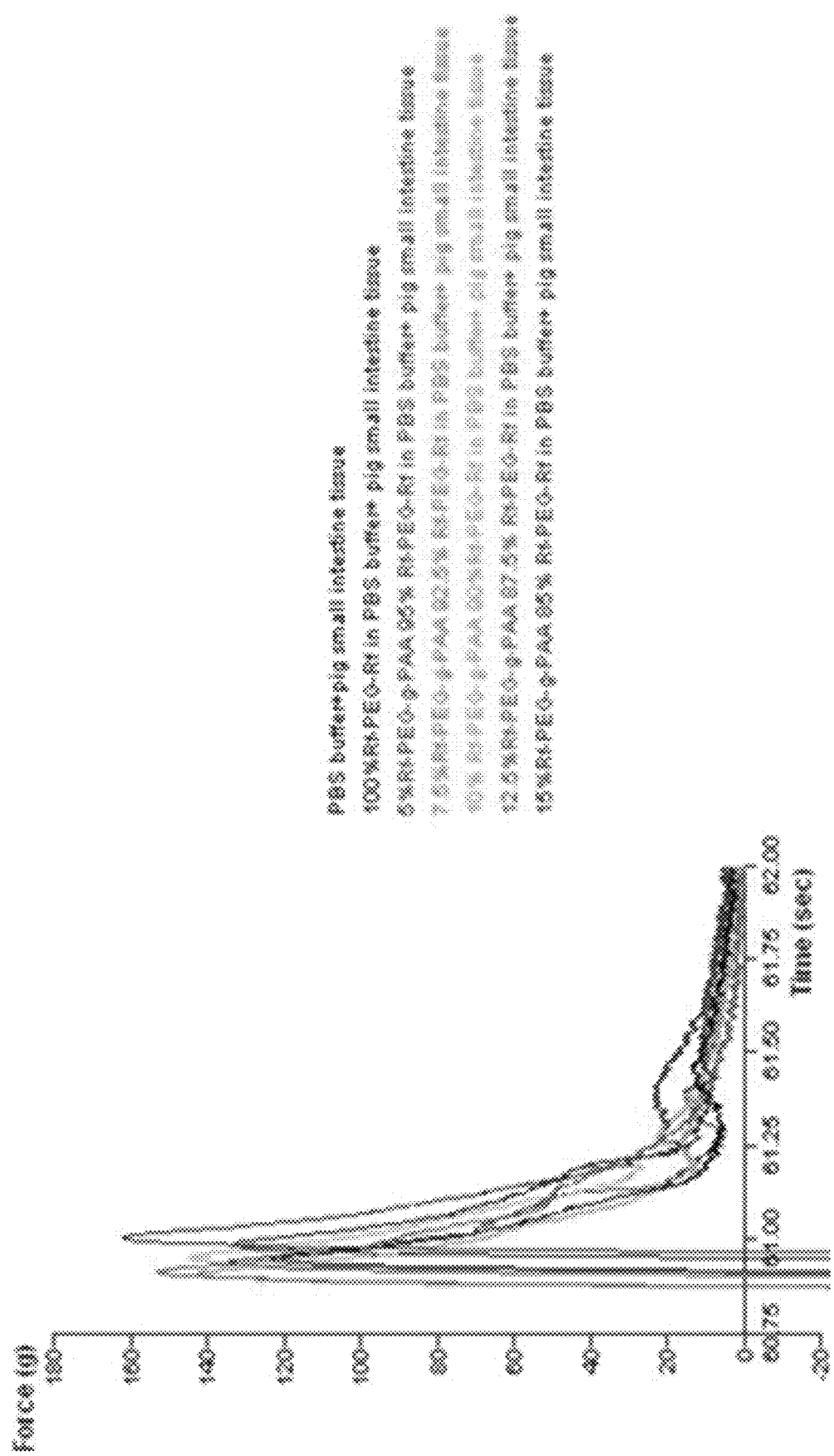
FIG. 24 shows force vs. time curves for various $R_f$-PEG-$R_f$/$R_f$-PEG-g-PAA co-hydrogels in PBS buffer interacting with pig small intestine.
Figure 25:
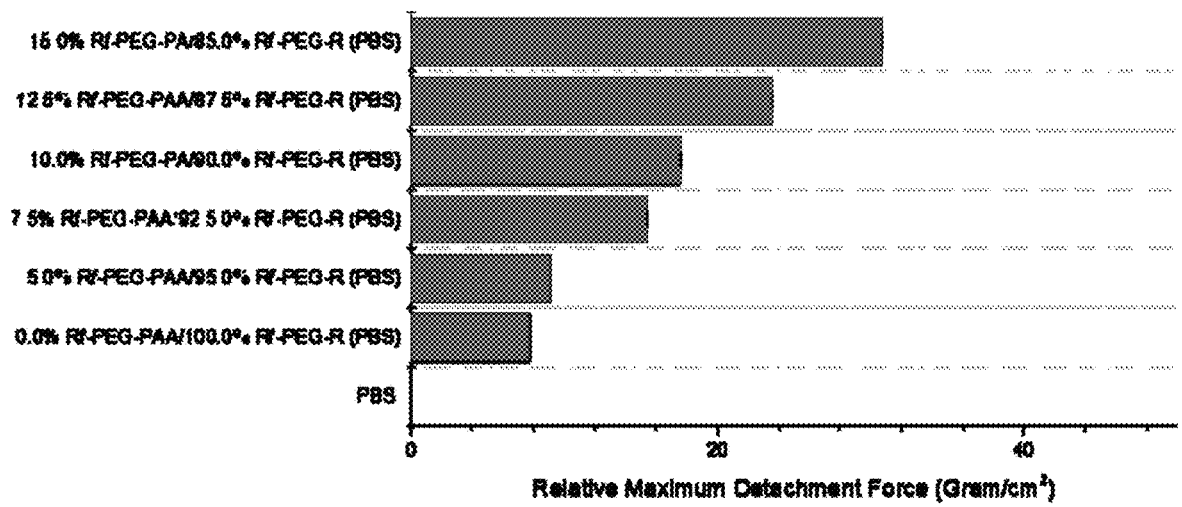
FIG. 25 is a bar graph showing relative (to PBS) maximum detachment forces for various $R_f$-PEG-$R_f$/$R_f$-PEG-g-PAA in PBS buffer with pig small intestine.

FIG. 24 shows force vs. time curves for various $R_f$-PEG-$R_f$/$R_f$-PEG-g-PAA co-hydrogels in PBS buffer interacting with pig small intestine. FIG. 25 is a bar graph showing relative (to PBS) maximum detachment forces for various $R_f$-PEG-$R_f$/$R_f$-PEG-g-PAA in PBS buffer with pig small intestine. The present $R_f$-PEG-$R_f$-PEG-g-PAA co-hydrogels showed a larger maximum detachment force relative to the $R_f$-PEG-$R_f$ hydrogel alone in the PBS buffer, significantly so at proportions of the $R_f$-PEG-g-PAA greater than 5%.

Figure 27:
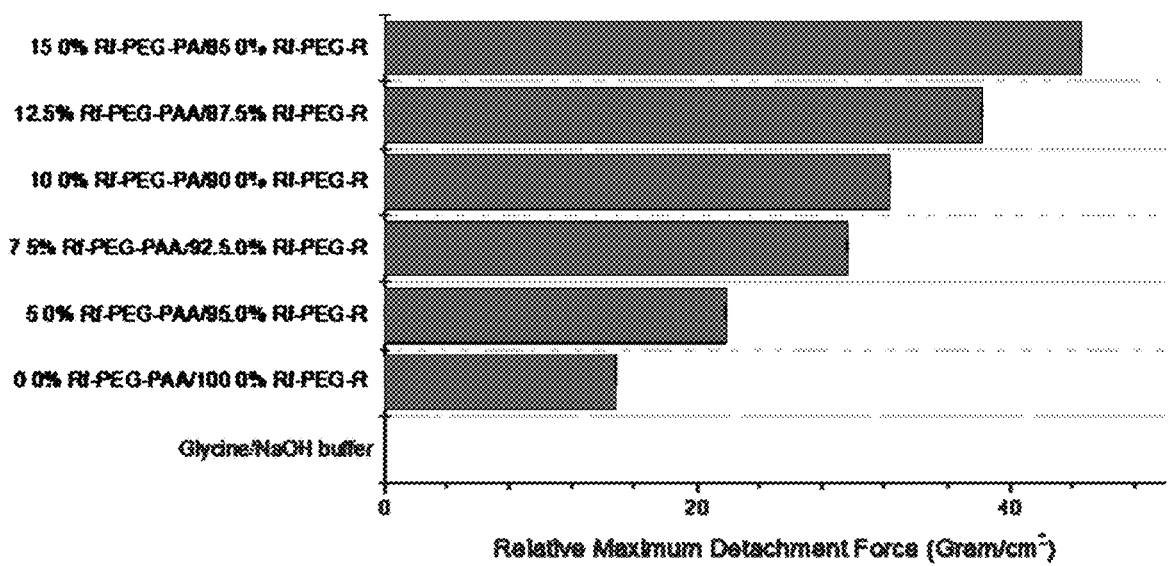
FIG. 27 is a bar graph showing relative (to glycine/NaOH buffer) maximum detachment forces for various $R_f$-PEG-$R_f$/$R_f$-PEG-g-PAA in glycine/NaOH buffer interacting with pig small intestine.
Figure 26:
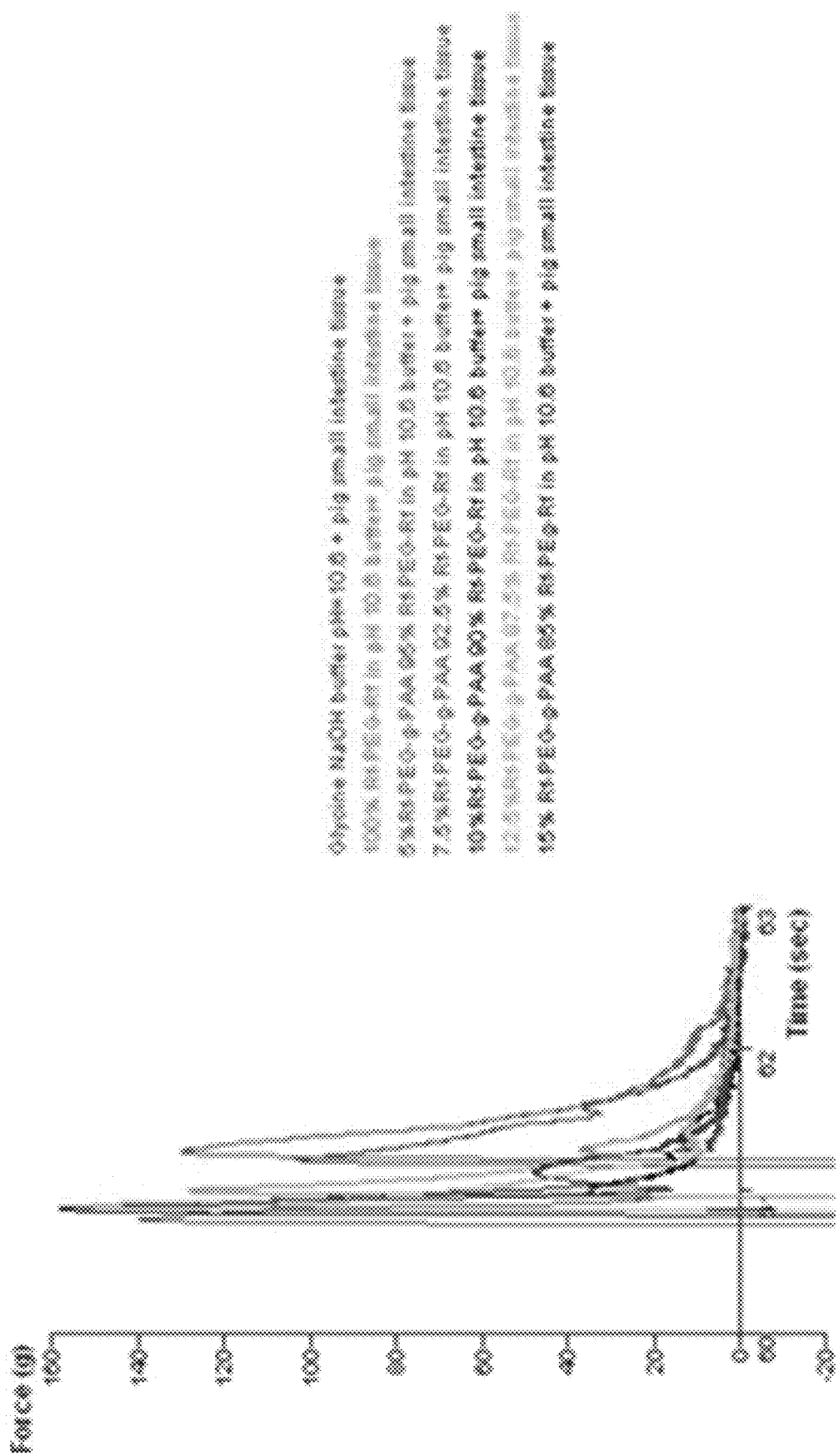
FIG. 26 shows force vs. time curves for various $R_f$-PEG-$R_f$/$R_f$-PEG-g-PAA co-hydrogels in glycine/NaOH buffer with pig small intestine.

FIG. 26 shows force vs. time curves for various $R_f$-PEG-$R_f$/$R_f$-PEG-g-PAA co-hydrogels in glycine/NaOH buffer with pig small intestine. FIG. 27 is a bar graph showing relative (to glycine/NaOH buffer) maximum detachment forces for various $R_f$-PEG-$R_f$/$R_f$-PEG-g-PAA in glycine/NaOH buffer interacting with pig small intestine. The present $R_f$-PEG-$R_f$/$R_f$-PEG-g-PAA co-hydrogels showed a larger maximum detachment force relative to the $R_f$-PEG-$R_f$ hydrogel alone in the glycine/NaOH buffer at all proportions of the $R_f$-PEG-g-PAA tested.

Figure 28:
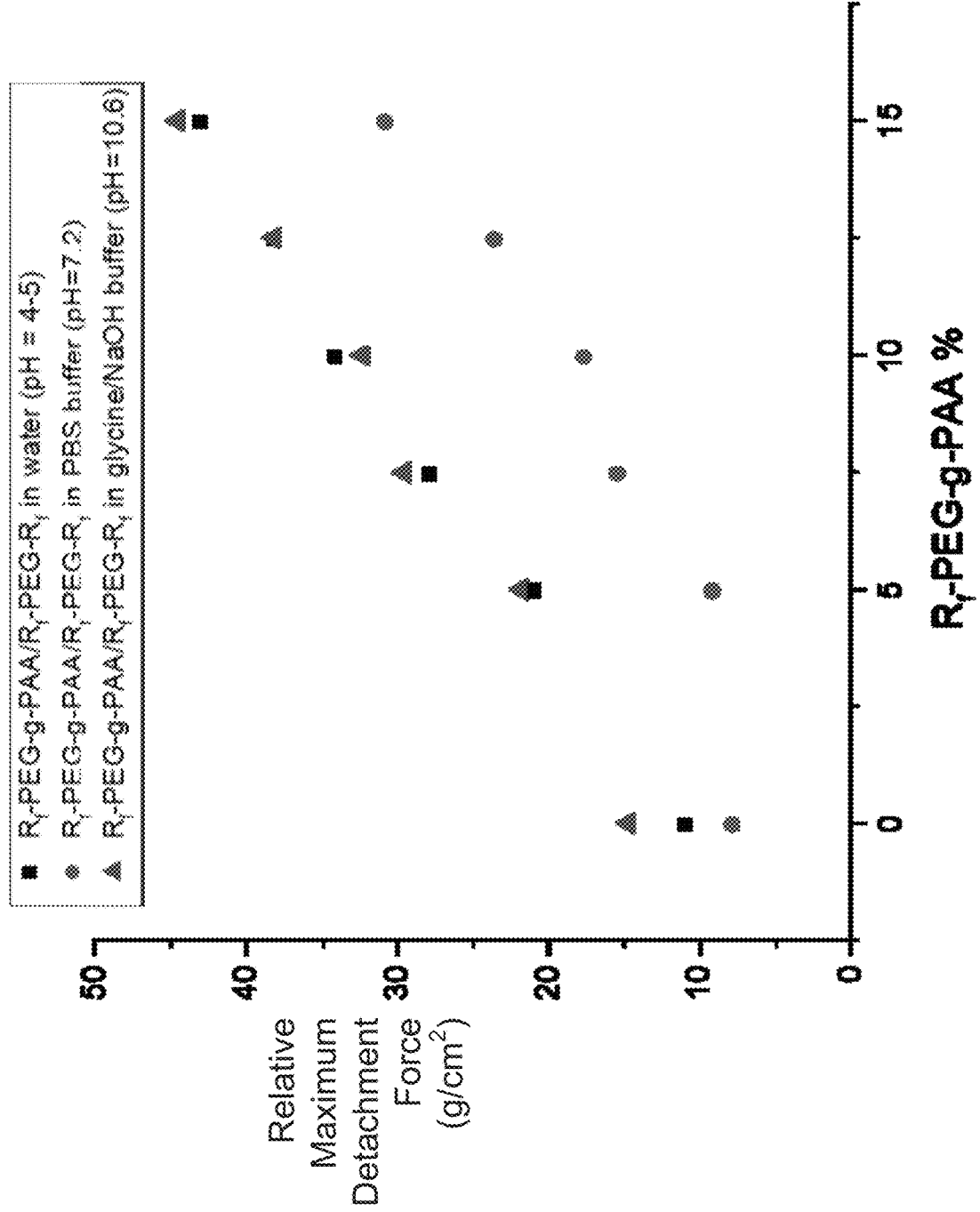
FIG. 28 is a graph comparing the MDFs of the interactions between the $R_f$-PEG-$R_f$/$R_f$-PEG-g-PAA hydrogel (in different buffers) surfaces and the pig small intestine surfaces.
Figure 29:
FIG. 29 shows a mechanism for transferring RAFT agent fragments during a chain-transfer process.
Figure 30:
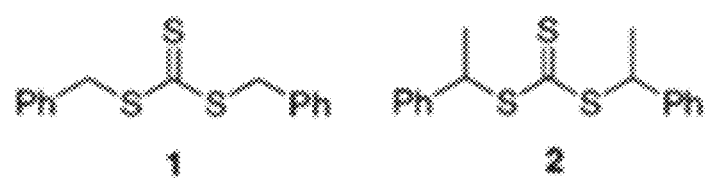
FIG. 30 shows the chemical structure of the chain transfer agents trithiocarbonic acid dibenzyl ester 1 and trithiocarbonic acid bis(1-phenylethyl) ester 2.
Figure 33:
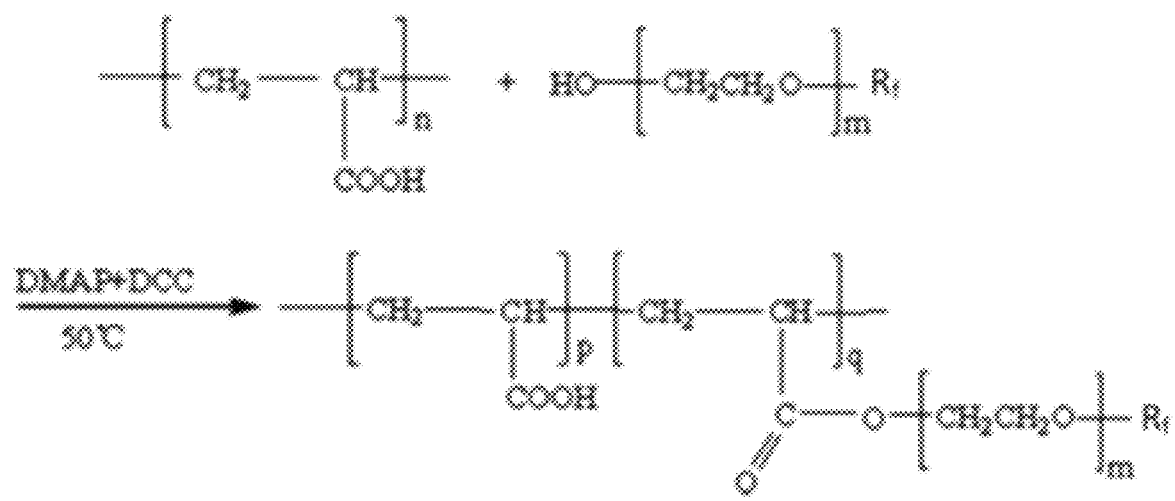
FIG. 33 shows an exemplary synthetic scheme for Steglich esterification of $R_f$-PEG-OH with PAA.
Figure 31:
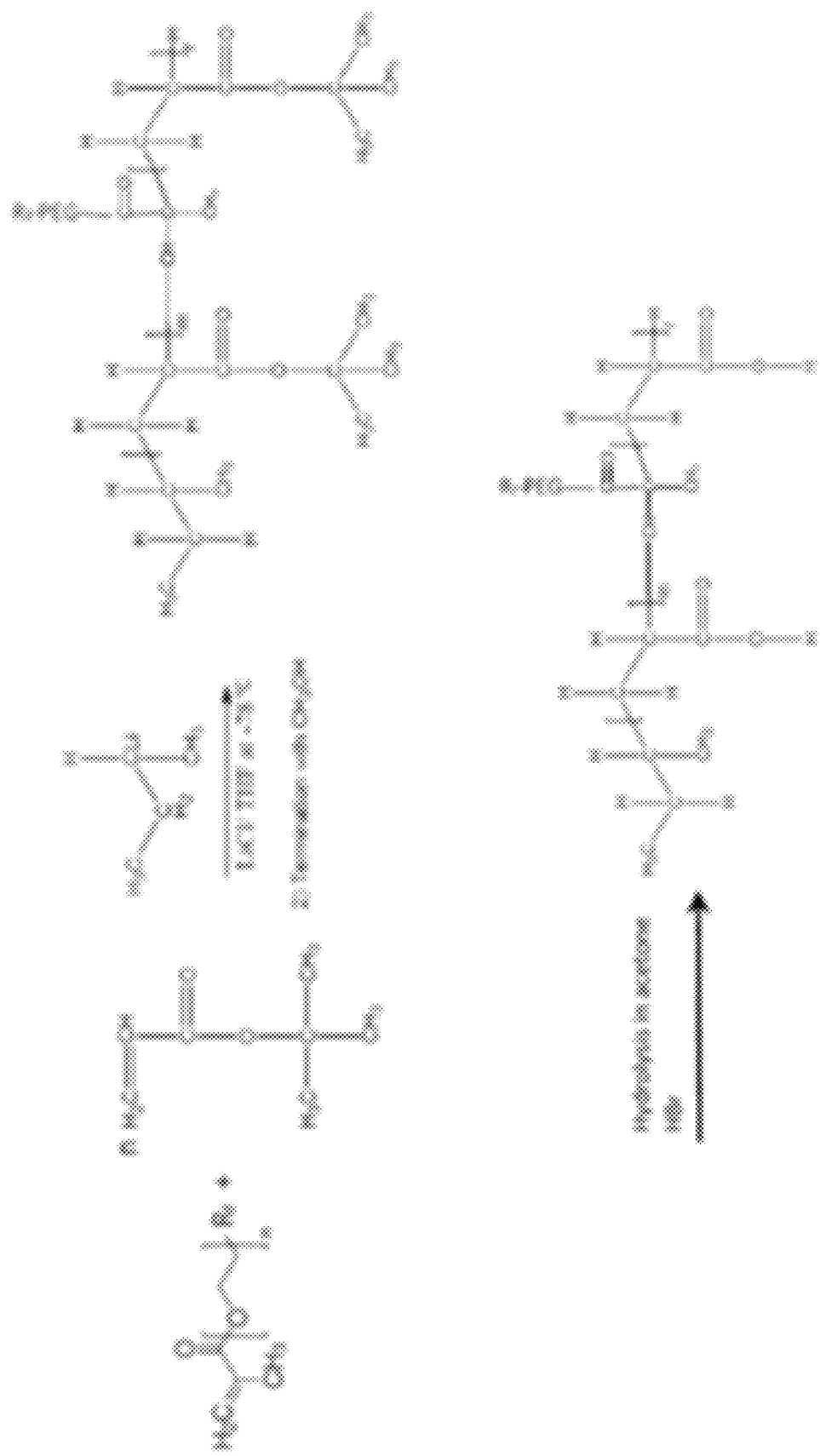
FIG. 31 shows an exemplary scheme using ionic polymerization to synthesize $R_f$-PEG-b-PAA.
Figure 32:
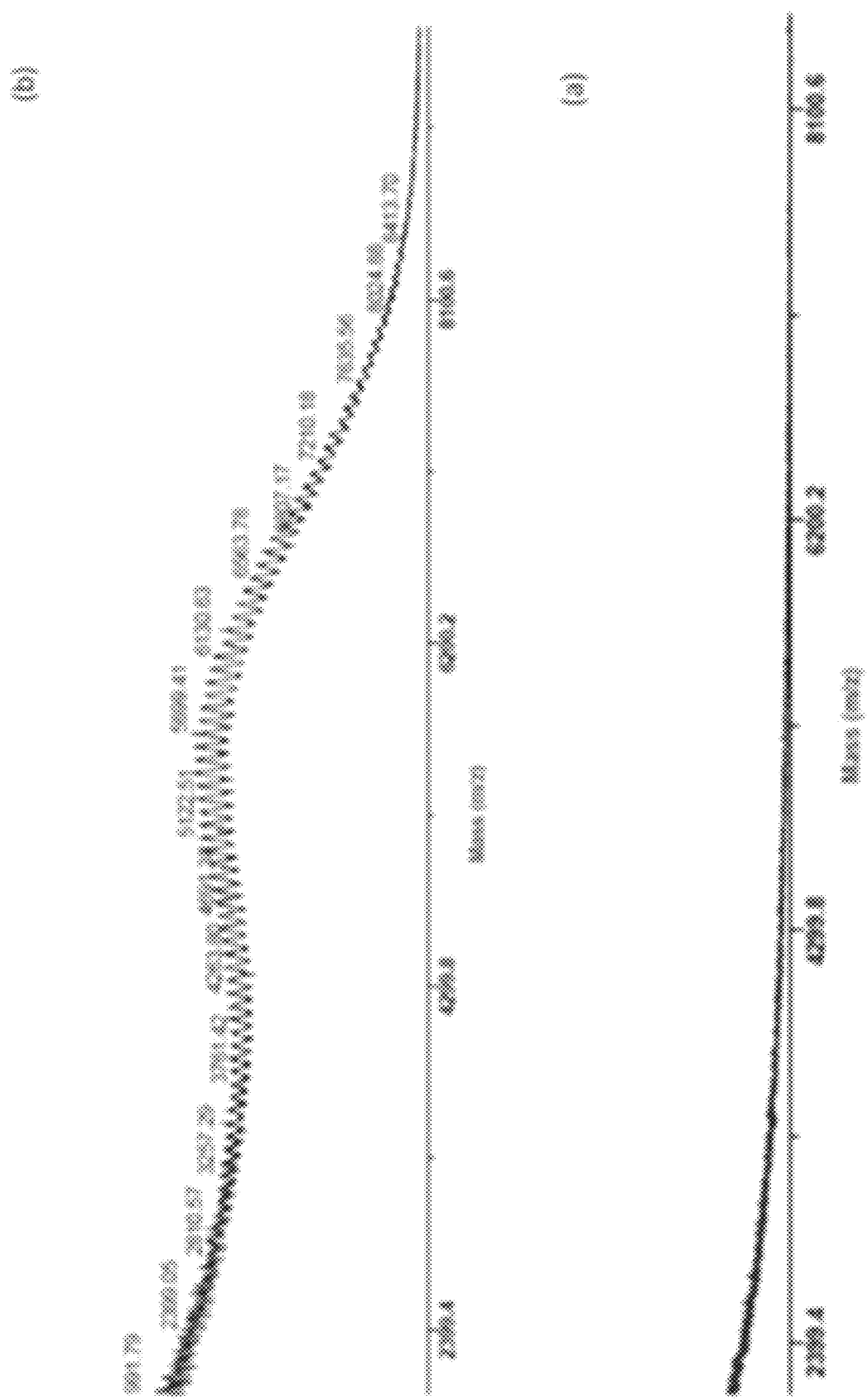
FIG. 32 shows MALDI-TOF mass spectra of (a) the IAA MALIN TOF matrix and (b) PAA prepared by RAFT polymerization, each using a negative charge mode.
Figure 34:
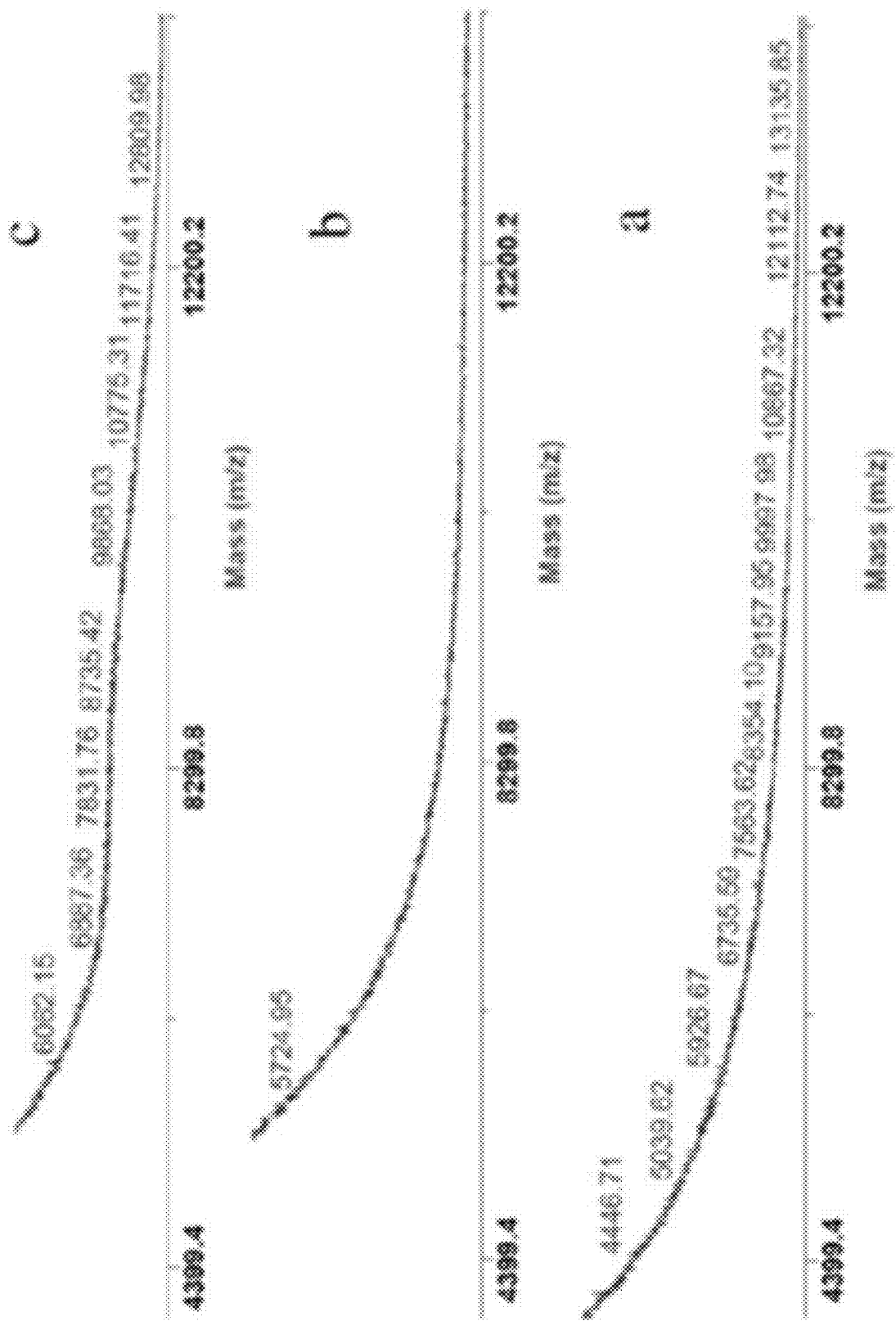
FIG. 34 shows a MALDI-TOF mass spectrum of another exemplary $R_f$-PEG-g-PAA described in the experimental section below.

FIG. 28 shows a comparison of the relative MDFs of and/or in the interactions between the $R_f$-PEG-$R_f$/$R_f$-PEG-g-PAA hydrogels (in the different buffers) and the pig small intestine surface. It shows that the adhesion forces are the largest when the co-hydrogels were prepared in the glycine/NaOH buffer and in water, and those in the PBS buffer are the smallest. The present co-hydrogels show sensitivity to and/or in mucoadhesion; that is, the mucoadhesion increases as the pH moves away from 7.

Figure 20A:
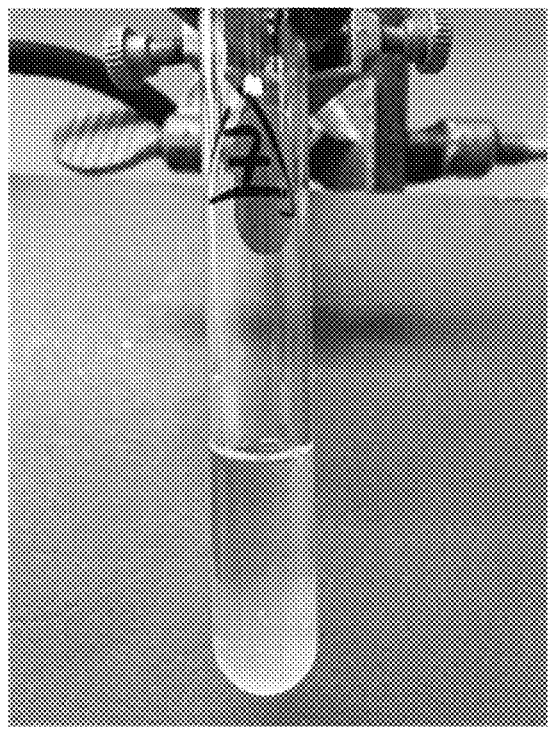
FIGS. 20A-F show photos of the two-phase coexistence of exemplary 5% $R_f$-PEG-PAA/95% $R_f$-PEG-$R_f$ and 10% $R_f$-PEG-PAA/90% $R_f$-PEG-$R_f$ sol-gels after being immersed in various aqueous media at 37° C.
Figure 20B:
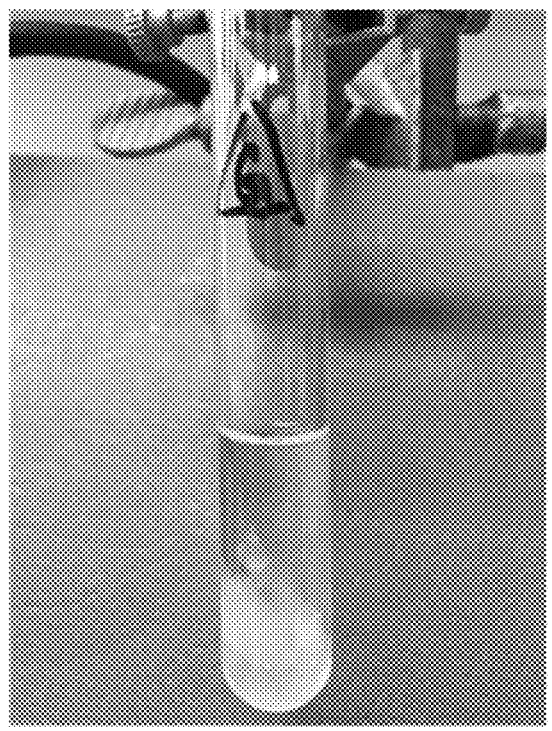

Sol-Gel Two-Phase Coexistence 70 mg 5% $R_f$-PEG-PAA/95% $R_f$-PEG-$R_f$, and 10% $R_f$-PEG-PAA/90% $R_f$-PEG-$R_f$ 90% homogeneous solid mixtures were made by dissolving them in methanol, and then lyophilizing them overnight. The polymer mixtures were then compressed to tablets (9.525 mm in diameter) under a pressure of 400 psi. Each tablet was put into a 13 mm inner diameter glass tube, and immersed in the above-described PBS buffer to form a 5 wt % mixture in PBS (pH=7.2). They were then placed in an incubator at 37° C. The expansion of the gel phase was observed. The gel phase and the sol phase eventually reached equilibrium after many days. FIGS. 20A-B show photos of the sol-gel two-phase coexistences of the 5% $R_f$-PEG-PAA/95% $R_f$-PEG-$R_f$ (FIG. 20A) and 10% $R_f$-PEG-PAA/90% $R_f$-PEG-$R_f$ (FIG. 20B) samples after immersion in PBS buffer at 37° C. for 11 days in the incubator.

Figure 20C:
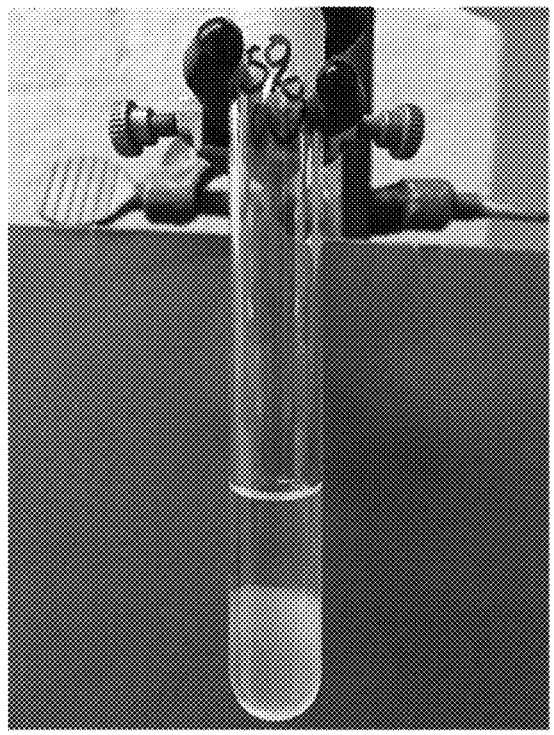
Figure 20D:
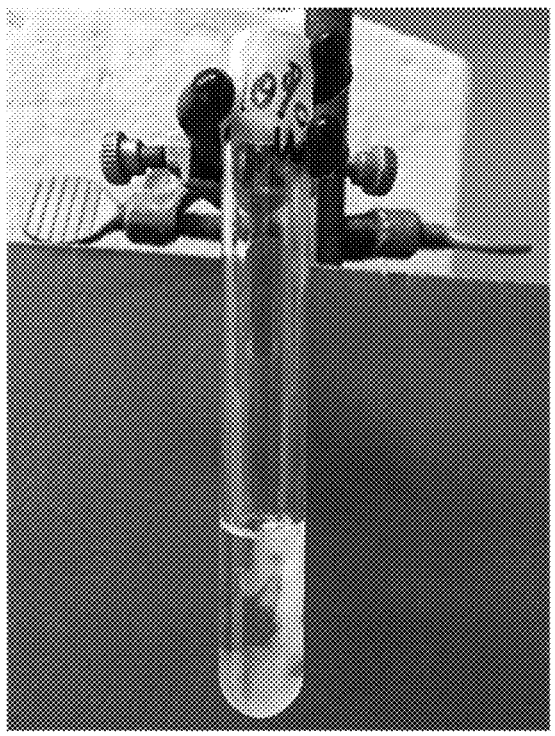
Figure 20E:
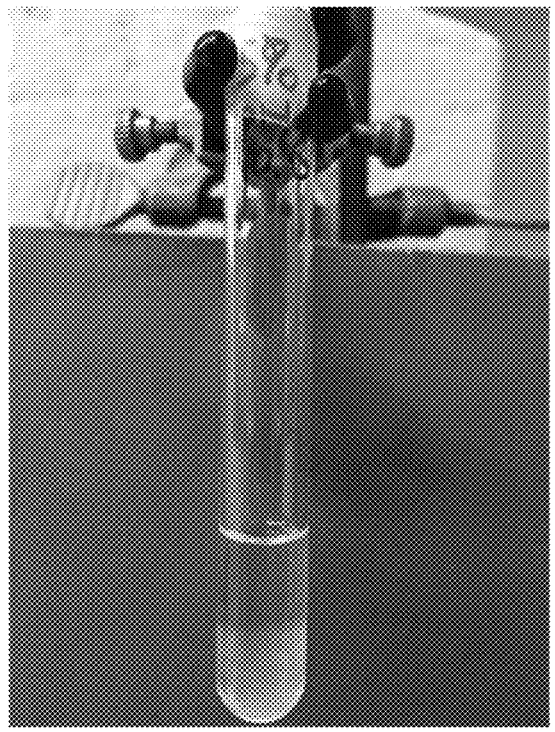
Figure 20F:
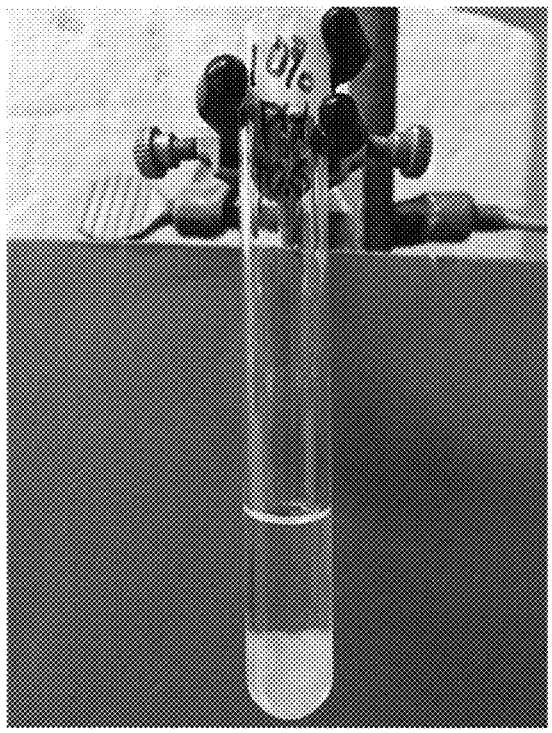

The experiments were repeated using water and glycine/sodium hydroxide buffer, respectively, under the same conditions. FIGS. 20C-D show photos after 16 days' incubation for 5% $R_f$-PEG-PAA/95% $R_f$-PEG-$R_f$ in water and 10% $R_f$-PEG-PAA/90% $R_f$-PEG-$R_f$ in water, respectively. FIGS. 20E-F show photos after 16 days' incubation for 5% $R_f$-PEG-PAA/95% $R_f$-PEG-$R_f$ in the glycine/sodium hydroxide buffer and 10% $R_f$-PEG-PAA/90% $R_f$-PEG-$R_f$ in the glycine/sodium hydroxide buffer, respectively. These results demonstrate that the sol-gel two-phase co-hydrogel for these samples were retained after a very long incubation time in different buffers.

Other $R_f$-PEG-PAA/$R_f$-PEG-$R_f$ Analogs

It has been reported that $R_f$-PEG-$R_f$ polymers with the compositions of 10KC8, 10KC10, 6KC6, and 6KC8 possess the properties of sol-gel two-phase coexistence and surface erosion (Tae G, Kornfield J A, Hubbell J A, Johannsmann D, Hogen-Esch T E: Hydrogels with Controlled, Surface Erosion Characteristics from Self-Assembly of Fluoroalkyl-Ended Poly(ethylene glycol), Macromolecules 2001, 34:6409-6419; Tae G, Komfield J A, Hubbell J A, Lal J: Ordering Transitions of Fluoroalkyl-Ended Poly(ethylene glycol): Rheology and SANS, Macromolecules 2002, 35:4448-4457). Therefore, the combination of these $R_f$-PEG-$R_f$ polymers with $R_f$-PEG-PAA can also form co-hydrogel systems with the properties described herein.

The sizes and/or molecular weights of the $R_f$, PEG and PAA blocks can also be varied in the $R_f$-PEG-PAA polymer. In addition to the $R_f$-PEG-g-PAA copolymer, the linear block polymer $R_f$-PEG-PAA can have properties similar to the $R_f$-PEG-g-PAA polymer. The PAA block itself can be linear, star-shaped or dendrimeric, and in the latter two cases, there may be more than one PAA chain in the $R_f$-PEG-PAA polymer. To increase the association force of the $R_f$-PEG-PAA with $R_f$-PEG-$R_f$ micelles, the mucoadhesion promoter (e.g., the $R_f$-PEG-PAA) can be made with one or more additional $R_f$-PEG blocks, such as $R_f$-PEG-$R_f$-PEG-PAA or $R_f$-PEG-PAA-PEG-$R_f$.

The synthesis of the $R_f$-PEG-PAA is not restricted to the procedure described above. The $R_f$-PEG-PAA can also be synthesized by other methods, as described below.

RAFT Copolymerization of Acrylic Acid (AA) with $R_f$-PEG-ma

Reversible-addition-fragmentation chain-transfer radical (RAFT) polymerization was first discovered in 1998 by Le et al. (International/PCT Pat. Appl. No. WO 9801478 A1, the relevant portions of which are incorporated herein by reference). RAFT polymerization is essentially a free-radical polymerization to which a highly active dithioester transfer agent (the RAFT agent) is added. The RAFT agent fragments during the chain-transfer process that release a new radical and generate a new dithioester species via the addition-fragmentation mechanism are shown in FIG. 21 (Young R J, Ovell P A: Introduction to Polymers; CRC Press (2011), Boca Raton, London, New York). The chain radical R. becomes trapped after being added to the RAFT agent, and that chain remains dormant until released in a further addition-fragmentation chain-transfer process when another chain radical is added to the dithioester end-group. When a highly active RAFT agent is used in chain transfers at a level greatly exceeding the total number of primary radicals generated from the initiator, addition-fragmentation chain-transfer to dithioester groups becomes the dominant process. Thus, there is a low probability for bimolecular termination under such conditions.

RAFT polymerization has been applied to synthesize poly(acrylic acid) (PAA) using the chain transfer agents trithiocarbonic acid dibenzyl ester 1 and trithiocarbonic acid bis(1-phenylethyl) ester 2 as chain transfer agents (CTA) (FIG. 22) (Loiseau J, Doërr N, Suau J M, Egraz J B, Llauro M F, Ladavière C, Claverie J: Synthesis and Characterization of Poly(acrylic acid) Produced by RAFT Polymerization. Application as a Very Efficient Dispersant of $CaCO_3$, Kaolin, and $TiO_2$. Macromolecules 2003, 36:3066-3077). A similar method is used to synthesize $R_f$-PEG-g/b-PAA.

Briefly, a solution of AA monomers will be prepared with an AA concentration of 2.92 mol/L (25% w:w) in ethanol or 3.58 mol/L (25% w:w) in dioxane, and the ratio [AA]:[CTA]:[Initiator] may be, for example, 500:1:0.1 (Loiseau et al., Macromolecules 2003, 36:3066-3077). Under these conditions, Loiseau et al. reported that PAA having a Mn=8,850 Da and Mn=12,000 Da in ethanol and dioxane, respectively, were produced in 4 hours. After all AA monomers are consumed, a corresponding 1:1 molar amount of an $R_f$-PEG-ma (e.g., poly(ethylene glycol) monomethacrylate solution is added to produce an $R_f$-PEG-b-PAA polymer. $R_f$-PEG-g-

PAA can be produced by adding the AA monomer solution subsequently to the $R_f$-PEG-b-PAA polymer. Continuously, a comb-like polymer can be made by attaching (grafting) more than one $R_f$-PEGs to one PAA chain.

Polymers with other molecular weight distributions can be produced by varying the [AA]:[CTA]:[Initiator] ratio. Experimentally, the solutions are held in a 100 mL three neck flask connected to a cold-water condenser and degassed by gentle nitrogen bubbling. The flask is then brought to 80° C. The solution is protected by a nitrogen or argon atmosphere. Polymerization is initiated by adding the initiator (e.g., 4,4'-azobis[4-cyanovaleric acid]). Aliquots are regularly withdrawn to monitor molecular weight and conversion. At the end of polymerization, an excess amount of an aqueous solution of 10 M NaOH is added to neutralize the product and unreacted monomers and to cleave the dithio-terminated chains (pH>9). This mixture is stirred for 2 hours and then dried in vacuo.

RAFT polymerization has been carried out by the present inventors using AA monomers to demonstrate this method. The result is shown in FIG. 24(b), which is a MALDI TOF spectrum of PAA made by RAFT polymerization. It shows that a PAA polymer with an average molecular weight of 6.0 kDa was obtained. FIG. 24(a) shows the MALDI-TOF spectra of the IAA MALDI TOF matrix, in which a negative charge mode was used.

Living Anionic Copolymerization of Tert-Butyl Acrylate with $R_f$-PEG-ma Followed by Hydrolysis An important feature of anionic polymerization is the absence of an inherent termination process due to charge repulsion. Organolithium compounds (e.g. butyllithium [BuLi]) are the most widely used organometallic initiators, although electron transfer initiation has also been used. The initiation is rapid if the reaction is performed in a polar solvent such as THF because the organolithium compound exists as a free species in a polar solvent. The reaction is pseudo-first-order since the concentration of the initiator is a constant for each particular reaction.

It has been proven that anionic polymerization produces polymers with a narrow molecular weight distribution (Szwarc M, Levy M, Milkovich R: Polymerization Initiated by Electron Transfer to Monomer. A New Method of Formation of Block Polymers, *J Am Chem Soc* 1956, 78:2656-2657; Nagasawa M: Thermodynamic and Hydrodynamic Properties of Polyelectrolytes, *J Polymer Sci* 1975, Symp. 49:1-29). Kitano and his colleagues studied the conditions of the anionic polymerization of tert-butyl acrylate (tBA) to produce poly(acrylic acid) with narrow molecular weight distribution (*Polymer Journal* 1977, 9 (2):153-159). They demonstrated that the monomer can be anionically polymerized with n-BuLi in THF at −78° C. The polymer obtained was hydrolyzed with hydrobromic acid without degradation.

Teyssié's research group published a series papers to illustrate that anionic polymerization of acrylic monomers can be used to synthesize di- and tri-block copolymers (Varshney S K, Jacobs C, Hautekeer J-P, Bayard P, Jérôme R, Fayt R, Teyssié P: Anionic Polymerization of Acrylic Monomers. 6. Synthesis, Characterization, and Modification of Poly(methyl methacrylate)-Poly(tert-butyl acrylate) Di- and Triblock Copolymers, *Macromolecules* 1991, 24:4997-5000; Varshney S K, Hautekeer J P, Fayt R, Jérôme R, Teyssié P: Anionic Polymerization of (Meth)acrylic Monomers. 4. Effect of Lithium Salts as Ligands on the "Living" Polymerization of Methyl Methacrylate Using Monofunctional Initiators, *Macromolecules* 1990, 23:2618-2622; Wang J-S, Jérôme R, Bayard P, Patin M, Teyssié P: Anionic Polymerization of Acrylic Monomers. 16. Living Anionic Copolymerization of Methyl Methacrylate and tert-Butyl Acrylate as Promoted by Lithium 2-(2-Methoxyethoxy) Ethoxide, *Macromolecules* 1994, 27:4635-4638). In one of their works, poly(methyl methacrylate)-b-poly (tert-butyl acrylate) (PMMA-b-PtBA) copolymers were successfully synthesized by sequential anionic polymerization of methyl methacrylate (MMA) and tert-butyl acrylate (tBA) in THF at −78° C. Mono- and bifunctional initiators based on alkali metals were used for the reactions. They found that when the initiators were modified by LiCl as a ligand, the polymerization of each block was living; the molecular weight and composition were predictable and the molecular weight distribution was narrow.

As shown in FIG. 23 (an ionic polymerization scheme to synthesize $R_f$-PEG-PAA polymers), similar strategies are used to synthesize $R_f$-PEG-b-PAA and $R_f$-PEG-g-PAA copolymers with relatively controlled block sizes. Briefly, a Schlenk line is used to control operations and the reaction itself under an inert atmosphere, and anhydrous solvents and reagents are used. The anionic polymerization is carried out with n-BuLi or s-BuLi as initiator and LiCl as a ligand in THF at −78° C. a THF solution of tBA monomer is added to the THF solution of n-BuLi held in a three-neck round-bottom flask under homogeneous stirring using a magnetic bar. Since the rate of anionic polymerization of tBA is very fast, the concentration of the monomer solution is kept low (e.g. 0.2 mol/L). After the monomers are consumed, the THF solution of $R_f$-PEG-ma is added to the flask. After the reaction is completed, the polymerization is terminated by pouring excess methanol into the flask, which will also precipitate the intermediate product ($R_f$-PEG-b-PtBA). The precipitate is washed with fresh methanol and dried in vacuo. Grafted $R_f$-PEG-PtBA can also be synthesized if THF solution of the tBA monomer is added after the complete transfer of the polymerization to $R_f$-PEG-ma. Transfer of polymerization to $R_f$-PEG-ma may be slow due to slow diffusions of both PtBA and $R_f$-PEG-ma. Thus, one may also initiate $R_f$-PEG-ma, and then add the tBA monomer solution to the reactor for making the $R_f$-PEG-b-PAA. The molar mass distribution of the PtBA block is controlled by the molar ratio of the tBA monomer to the initiator, but this is generally determined by experiment because possible impurities may also react with the initiator (see, e.g., Varshney et al., *Macromolecules* 1990, 23:2618-2622).

To obtain the final product, $R_f$-PEG-b/g-PAA, the $R_f$-PEG-b/g-PtBA copolymer is dissolved in acetone (e.g. 1 g/100 mL) and warmed up to 60° C. A small amount of concentrated hydrobromic acid is added to the solution under stirring using a magnetic bar. After several hours, the acetone is distilled off, and an aqueous solution of sodium hydroxide is added to the remaining polymer solution until the pH of the solution becomes greater than 10. A $R_f$-PEG-b/g-PAA polymer salt is precipitated by adding methanol to the basic solution. A more hydrophobic solvent can be used if methanol does not precipitate the product well. After separation, the precipitate is purified by washing with methanol and water, then drying in vacuo. The product is dissolved in water, and converted to $R_f$-PEG-b/g-PAA through passing through an appropriate ion-exchange resin. The above hydrolysis procedure follows the process disclosed by Kitano et al. (*Polymer Journal* 1977, 9 (2):153-159).

Graft Copolymer of $R_f$-PEG-OH with PAA by Steglich Esterification

Steglich esterification (Neises B, Steglich W: Simple Method for the Esterification of Carboxylic Acids, *Angew*

*Chem Int Ed* 1978, 4:1067-1068) has been used by Luo et al. to synthesize a poly(acrylic acid)-g-methoxy poly(ethylene oxide) comb-like copolymer (Luo Y, Ran Q, Wu S, Shen J: Synthesis and Characterization of a Poly(acrylic acid)-graft-Methoxy Poly(ethylene oxide) Comblike Copolymer, *Journal of Applied Polymer Science* 2008, 109:3286-3291). A similar method is used to synthesize $R_f$-PEG-g-PAA.

In the present method, dicyclohexylcarbodiimide (DCC) is used as a coupling reagent, and 4-dimethylaminopyridine (DMAP) as a catalyst. Water generated in the reaction reacts with DCC by forming a corresponding urea compound, dicyclohexyl urea (DCU). As shown in FIG. 25, a similar method is used to synthesize $R_f$-PEG-g-PAA.

Briefly, freshly dried PAA (commercially available) and the mixture of $R_f$-PEG-$R_f$ and $R_f$-PEG-OH (PAA:$R_f$-PEG-OH molar ratio>1:1) is dissolved in tetrahydrofuran (THF) in a flask. DCC and DMAP is added under stirring. The reaction proceeds at 50° C. under argon gas for several days. Then, the solution is filtered to remove the precipitated DCU. $CHCl_3$ (chloroform) is added to precipitate the remaining PAA. Rotary evaporation is used to condense the product.

FIG. 26 shows the MALDI-TOF spectrum of the $RR_f$-PEG-g-PAA. An m/z distribution around 8.5 kDa in the spectrum of FIG. 26(c) is the sum of the molar mass of the PAA (2 kDa) and the $R_f$-PEG-OH (6.5 kDa). We used the mixture of $R_f$-PEG-$R_f$ and $R_f$-PEG-OH with a molar ratio of $R_f$-alcohol/PEG=1.7/1.0 in the synthesis. Thus, there is remaining $R_f$-PEG-$R_f$ in the product. However, the negative charge mode of the MALDI-TOF method does not show the $R_f$-PEG-$R_f$. $R_f$-PEG-$R_f$ is observed in the positive mode spectrum (not shown). To obtain pure $R_f$-PEG-g-PAA from the mixture of $R_f$-PEG-g-PAA and $R_f$-PEG-$R_f$, the solution of the product is dried using a rotary evaporator and neutralized with MOH solution. The negatively charged PAA block may not allow the $R_f$-PEG-g-PAA to be dissolved in glyme or methanol, while $R_f$-PEG-$R_f$ can be. Using this method, a comb-like $R_f$-PEG-g-PAA can also be synthesized when the $R_f$-PEG-OH:PAA molar ratio is larger than 2:1.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A polymer mixture, comprising:
   a) a block copolymer of the formula $R_f^1$-PEG-PAA, wherein:
      (i) $R_f^1$ comprises a perfluoroalkyl group having at least 3 carbon atoms, bound to an ether oxygen atom directly or through a substituted or unsubstituted alkylene group;
      (ii) PEG is a poly(alkylene glycol) unit having a weight average molecular weight or number average molecular weight of from 1 to 20 kDa; and
      (iii) PAA is one or more poly([meth]acrylic acid) units having a total weight average molecular weight or number average molecular weight of from 0.3 to 10 kDa; and
   b) a second perfluoroalkyl-terminated PEG polymer having the formula $R_f^2$-PEG-$R_f^3$, where $R_f^2$ and $R_f^3$ each independently comprises a perfluoroalkyl group having at least 3 carbon atoms, bound to an ether oxygen atom directly or through a substituted or unsubstituted alkylene group.

2. The polymer mixture of claim 1, wherein $R_f$ has the formula $(C_nF_{2n+1})(C_aH_{2a})O—$, where n is an integer of at least 4, and a is an integer of at least 1.

3. The polymer mixture of claim 2, wherein n is an integer of at most 20, and a is an integer of at most 2.

4. The polymer mixture of claim 1, wherein the PEG consists essentially of poly(ethylene glycol).

5. The polymer mixture of claim 4, wherein the PEG has the number average molecular weight, and the number average molecular weight is from 3 to 10 kDa.

6. The polymer mixture of claim 1, wherein the PAA consists essentially of units of the formula $(—R^1CHCH(CO_2R^2))—_p$, where $R^1$ is H or $CH_3$, $R^2$ is H or an alkali metal or ammonium ion, and p has an average value providing the total weight average molecular weight or number average molecular weight.

7. The polymer mixture of claim 6, wherein the PAA has the number average molecular weight, and the number average molecular weight is from 0.5 to 3 kDa.

8. The polymer mixture of claim 1, wherein the block copolymer and the second perfluoroalkyl-terminated PEG polymer are present in a ratio of from 1:99 to 25:75.

9. A co-hydrogel, comprising the mixture of claim 1 in an aqueous environment.

10. A drug delivery vehicle comprising the mixture of claim 1.

11. The drug delivery vehicle of claim 10, further comprising a pharmaceutically active drug.

12. A method of forming a sol-gel two-phase co-hydrogel, comprising:
   a) combining the polymer mixture of claim 1 with an aqueous environment; and
   b) annealing the polymer mixture and the aqueous environment to form the sol-gel two-phase co-hydrogel.

13. The method of claim 12, wherein the aqueous environment consists essentially of water or an aqueous buffer.

14. The method of claim 12, wherein the sol-gel two-phase co-hydrogel has a mucoadhesion greater than that of an otherwise identical hydrogel containing an equal or equivalent amount of the second perfluoroalkyl-terminated PEG polymer.

15. A method of forming a drug delivery vehicle, comprising:
   a) combining the polymer mixture of claim 1 with an aqueous environment and a drug; and
   b) annealing the polymer mixture, the aqueous environment and the drug to form the drug delivery vehicle.

16. The method of claim 15, wherein the drug is a pharmaceutically active compound that is stable in an aqueous sol-gel two-phase co-hydrogel.

17. A method of delivering a drug to a patient in need thereof, comprising:
   a) combining a drug delivery vehicle by the method of claim 15, the drug delivery vehicle including the drug; and
   b) administering a pharmaceutically effective amount of the drug to the patient by applying a corresponding amount of the drug delivery vehicle to a mucus membrane of the patient.

* * * * *